US012521537B2

(12) United States Patent
Skak et al.

(10) Patent No.: US 12,521,537 B2
(45) Date of Patent: Jan. 13, 2026

(54) ORAL DRUG DELIVERY DEVICE WITH COVER RELEASE

(71) Applicant: Biograil APS, Roskilde (DK)

(72) Inventors: Nikolaj Skak, Roskilde (DK); Raimo Urban Butzbacker, Roskilde (DK)

(73) Assignee: Biograil APS, Roskilde (DK)

( * ) Notice: Subject to any disclaimer, the term of this patent is extended or adjusted under 35 U.S.C. 154(b) by 0 days.

(21) Appl. No.: 19/192,037

(22) Filed: Apr. 28, 2025

(65) Prior Publication Data

US 2025/0332395 A1 Oct. 30, 2025

(30) Foreign Application Priority Data

Apr. 29, 2024 (DK) ........................... PA 2024 70124

(51) Int. Cl.
*A61M 37/00* (2006.01)

(52) U.S. Cl.
CPC ..... *A61M 37/00* (2013.01); *A61M 2037/0007* (2013.01); *A61M 2205/103* (2013.01)

(58) Field of Classification Search
CPC ............ A61M 37/00; A61M 2205/103; A61M 15/0031; A61M 5/2455; A61J 7/0053; A61J 1/202; A61J 1/2024; A61J 1/2027
See application file for complete search history.

(56) References Cited

U.S. PATENT DOCUMENTS

2014/0148758 A1* 5/2014 Iparraguirre ........ A61M 3/0262
604/87

FOREIGN PATENT DOCUMENTS

| | | | |
|---|---|---|---|
| DK | 2022 70525 | A1 | 6/2024 |
| JP | 2003-325438 | A | 11/2023 |
| WO | WO 2009/156919 | A1 | 12/2009 |
| WO | WO 2018/112240 | A1 | 6/2018 |
| WO | WO 2021/228826 | A1 | 11/2021 |
| WO | WO 2022/162149 | A1 | 8/2022 |
| WO | WO 2023/073174 | A1 | 5/2023 |
| WO | WO 2023/144159 | A1 | 8/2023 |
| WO | WO 2023/178354 | A1 | 9/2023 |
| WO | WO 2024/064603 | A1 | 3/2024 |

OTHER PUBLICATIONS

1st Technical Examination in PA 2024 70124 issued Oct. 28, 2024.
2nd Technical Examination in PA 2024 70124 issued Nov. 28, 2024.
3rd Technical Examination in PA 2024 70124 issued Feb. 26, 2025.
International Search Report for PCT/EP2025/061650 mailed on Jul. 17, 2025.

* cited by examiner

*Primary Examiner* — Nilay J Shah
(74) *Attorney, Agent, or Firm* — KNOBBE, MARTENS, OLSON, & BEAR, LLP

(57) ABSTRACT

An oral drug delivery device and a pharmaceutical composition is disclosed, the oral drug delivery having a longitudinal axis and extending from a first end to a second end, the oral drug delivery device comprising a cover; a body; a first attachment part having a first distal end and configured to deliver an active drug substance; and an actuator mechanism engaged with the first attachment part and configured to rotate the first attachment part about a first rotation axis forming an angle larger than 45 degrees with the longitudinal axis, the oral drug delivery device configured to break or weaken the cover prior to or during rotation of the first attachment part.

17 Claims, 23 Drawing Sheets

ORAL DRUG DELIVERY DEVICE WITH COVER RELEASE

CROSS REFERENCE TO RELATED APPLICATIONS

This application claims the benefit of priority to Danish Patent Application No. PA 2024 70124, filed on Apr. 29, 2024. The disclosure of the above-referenced application is hereby expressly incorporated by reference in its entirety.

FIELD

The present disclosure relates to an oral drug delivery device and in particular to a drug delivery device for oral administration. The oral drug delivery device is advantageously configured for delivery of an active drug substance in the gastrointestinal tract including the stomach and/or intestines, such as the small intestines and/or the large intestines (colon).

BACKGROUND

A number of low permeable and/or low water soluble active drug substances are currently delivered by i.e. subcutaneous, intradermal, intramuscular, rectal, vaginal or intravenous route. Oral administration has the potential for the widest patient acceptance and thus attempts to deliver low permeable and/or low water soluble active drug substances through the preferred oral route of administration has been tried but with limited success in particular due to lack of stability and limited absorption from the gastrointestinal tract.

Stability both relates to the stability of the active drug substance during manufacturing and storage of the delivery device, and to the stability of the active drug substance during the passage in the gastrointestinal tract before it become available for absorption.

Limited gastrointestinal absorption is due to the gastrointestinal wall barrier preventing active drug substance from being absorbed after oral dosing because of the low permeability of the active drug substance, which is for example due to pre-systemic metabolism, size and/or the charges and/or because of the water solubility of the active drug substance.

Multiple approaches to solve these stability and absorption challenges have been suggested, but an effective solution to the challenges remain unresolved.

SUMMARY

Thus, there is an unmet need to provide a drug delivery device, which is capable of efficiently delivering drug substances for absorption in the gastrointestinal tissue. More generally, there remains a need for drug products and methods that enable enhanced drug delivery, when drug products are administered orally to patients. i.e. via the gastrointestinal tract.

An oral drug delivery device is disclosed, the oral drug delivery device having or defining a longitudinal axis and extending from a first end to a second end, the oral drug delivery device comprising a cover; a body having a longitudinal axis and extending from a first end to a second end; a first attachment part or drug delivery member having a first distal end and configured to deliver an active drug substance; and an actuator mechanism engaged with the first attachment part/drug delivery member and configured to rotate the first attachment part/drug delivery member about a first rotation axis, e.g. forming an angle larger than 45 degrees with the longitudinal axis. The oral drug delivery device may be configured to break or weaken the cover, e.g. prior to and/or during rotation of the first attachment part/drug delivery member.

Further, a pharmaceutical composition is disclosed, the pharmaceutical composition comprising an active drug substance and an oral drug delivery device as described herein.

It is an advantage of the oral drug delivery device that the oral drug delivery device, such as via the first attachment part, can efficiently attach to a patient's tissue, such as for delivering an active drug substance to the patient. The oral drug delivery device can include minimum moving components, thereby reducing the number of parts that could break and/or fail during use. Further, certain implementations of the disclosed oral drug delivery device do not rely on multiple attachment parts, thereby improving the attachment ability of the oral drug delivery device to the patient, such as gastrointestinal tissue, e.g. in the stomach and/or intestines.

Advantageously, the present disclosure provides for a drug delivery device with improved rotation, e.g. rotation with higher force, of the first attachment part/drug delivery member in turn providing efficient insertion of the first attachment part(s)/drug delivery member in the tissue, such as gastrointestinal tissue, e.g. in the stomach and/or intestines.

Further, increased design flexibility of the oral drug delivery device is provided, e.g. by enabling higher flexibility in spike tip/distal end insertion angle in the tissue and/or larger reach of the spike by providing a larger spike tip to rotational axis center distance.

Other advantages of the present disclosure include simplicity in design, improved manufacture, large spike, miniaturization, small space footprint in turn allowing for more volume and flexibility of high load device.

BRIEF DESCRIPTION OF THE DRAWINGS

The above and other features and advantages of the present invention will become readily apparent to those skilled in the art by the following detailed description of example embodiments thereof with reference to the attached drawings, in which.

DETAILED DESCRIPTION

Figure 1A:
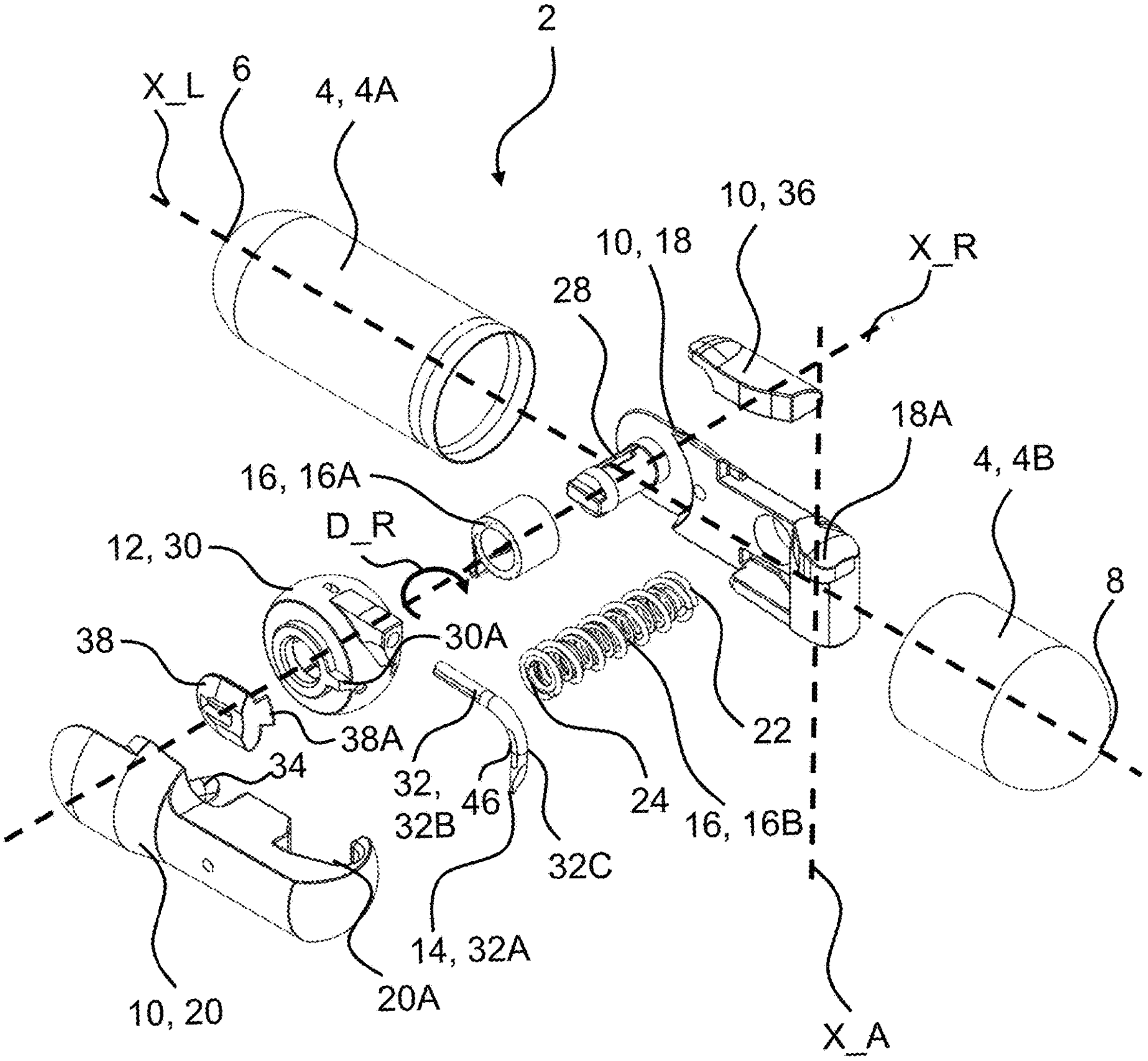
FIGS. 1A-1E show different views of an example oral drug delivery device.

Various example embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments and the functionalities associated therewith. They are not intended as an exhaustive description of the invention or as a limitation on the scope of the invention or the physical appearance of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Disclosed herein is an oral drug delivery device also denoted drug delivery device. In other words, a drug delivery device configured for oral administration is provided. The oral drug delivery device comprises a body having a longitudinal axis and extending from a first end to a second end.

In one or more examples, an oral drug delivery device is disclosed, the oral drug delivery device comprising a cover; a body having a longitudinal axis and extending from a first end to a second end; a first attachment part having a first distal end and configured to deliver an active drug substance; and an actuator mechanism engaged with the first attachment part and configured to rotate the first attachment part about a first rotation axis forming an angle larger than 45 degrees with the longitudinal axis, the oral drug delivery device configured to break or weaken the cover prior to or during rotation of the first attachment part.

In one or more examples, an oral drug delivery device is disclosed, the oral drug delivery device comprising a cover; a body having a longitudinal axis and extending from a first end to a second end; a drug delivery member having a first distal end and configured to deliver an active drug substance; and an actuator mechanism engaged with the drug delivery member and configured to rotate the drug delivery member about a first rotation axis forming an angle larger than 45 degrees with the longitudinal axis, the oral drug delivery device configured to break or weaken the cover prior to or during rotation of the drug delivery member.

The oral drug delivery device may have an initial configuration. The initial configuration may be an initial position and/or an initial state, such as when the oral drug delivery device is taken into a patient, such as via swallowing. The initial configuration can be a configuration before any actuation of the actuator mechanism, e.g. first actuator and/or second actuator of the oral drug delivery device. The initial configuration can be when the first attachment part/drug delivery member and/or the body parts, such as first body part, second body part, and optionally third body part, are in their initial position.

The oral drug delivery device may have a size and geometry designed to fit into a pharmaceutical composition for oral administration. As used herein, drug delivery device refers to an oral drug delivery device unless otherwise stated.

The oral drug delivery device may be configured to be taken into the body via the oral orifice. For example, the oral drug delivery device may be configured to be taken into the body in an initial configuration, e.g., when the first attachment part/drug delivery member and/or body parts are in their respective initial position. Thus, the outer dimensions of the oral drug delivery device may be small enough for a user to swallow, such as a size 00, a size 0, or a size 000. The oral drug delivery device may be adapted to carry a drug substance, e.g., an active drug substance, into the body of the user, via the digestive system, so that the drug delivery device may e.g., travel from the mouth of the user into the stomach, via the oesophagus. The oral drug delivery device may be configured to further travel into the intestines from the stomach, and may optionally travel into the bowels and out through the rectum. The drug delivery device may have a length in the range from 10 mm to 30 mm.

The oral drug delivery device may be configured to deliver the drug in any part of the digestive system of the user, where in one example it may be configured to deliver a drug substance into the stomach of the user. In another example, the oral drug delivery device may be adapted to initiate the drug delivery when the drug delivery device has passed the stomach and has entered the intestine of the user. In other words, the oral drug delivery device may be configured to attach to a wall of the stomach or a wall of the intestines, e.g., depending on the desired release position of the active drug substance. For example, the oral drug delivery device may be configured to transition from the initial configuration to an attached configuration (first attachment part in first position) to attach to the patient. In one or more example oral drug delivery devices, the oral drug delivery device is configured to transition from the initial configuration to the attached configuration as the first attachment part/drug delivery member transitions from the initial position to first position.

The first attachment part/drug delivery member may be configured to interact, such as penetrate, with the inner surface linings of the gastrointestinal tract, so that the oral drug delivery device, such as one or more parts of the oral drug delivery device, such as the first attachment part/drug delivery member, may e.g., be attached to the inner surface (mucous membrane) of the stomach, or alternatively to the mucous membrane of the intestines, such as in the attached configuration with the first attachment part/drug delivery member in the first position. The first attachment part may be configured to interact with the mucous membranes, e.g., in order to fix or attach the oral drug delivery device, e.g., for a period of time, inside the body of the user. By attaching the oral drug delivery device, it will allow a drug substance to be delivered into a part of the digestive system, in order to provide a drug substance to the body of the user. The first attachment part/drug delivery member may be configured to interact with, such as penetrate, the mucous membranes, e.g., in order to inject drug substance into the gastrointestinal tract wall.

In one or more example drug delivery devices, the oral drug delivery device may be configured with detachment capabilities. For example, the oral drug delivery device may be constructed in a way that releases the oral drug delivery device or at least parts thereof from internal tissues and/or internal surfaces, such as after distribution of the active drug substance.

The oral drug delivery device may have an attached or first configuration, e.g., attached position, attachment position, attachment configuration, attached state. The attached configuration may be understood as the configuration where the oral drug delivery device in use can attach or is attached to a surface in the patient, such as tissue, which can allow for delivery of the active drug substance. The attached configuration also denoted first configuration may be understood as the configuration where the oral drug delivery device in use can allow for delivery of the active drug substance, e.g. via the first attachment part or the drug delivery member. The attached configuration can be a configuration for attachment of the drug delivery device to the patient. The attached configuration may be different from the initial configuration. In the attached configuration, the oral drug delivery device may remain attached to the patient. In the attached configuration, the first attachment element/drug delivery member is in the first position. The attached configuration can be a configuration after an actuation of the actuator mechanism of the oral drug delivery device.

The cover may fully or at least partly encapsulate the body and/or the actuator mechanism. In one or more examples, the cover may encapsulate or cover at least 40% of the body, such as at least 70% of the body. In one or more examples, a part of the body are exposed, i.e. not covered by the cover. For example, an end of the body may be exposed.

The cover or shell may encapsulate the other parts of the drug delivery device. The cover may be made of a biodegradable material. The cover may be made of gelatine or a polymer material, such as a cellulosic polymer. In one or more examples, the cover is made of Hydroxypropyl methylcellulose also known as HPMC. The cover may be water-soluble.

Other suitable materials for the cover include compositions comprising one or more polymethacrylate-based copolymers also known as Eudragits, e.g. Eudragit E PO. The cover may be a multipart cover, such as a two-part capsule. The cover or capsule may comprise a plurality of layers, e.g. a first layer of a first material and a second layer of a second material different from the first material. Different layers and/or materials may allow for low friction properties and/or for controlling speed of disintegration/dissolution (i.e. at different pH conditions).

The cover may be made of a starch-based material, such as one or more polysaccharides. In one or more examples, the cover is made of Pullulan.

The cover may have a thickness in the range from 0.05 mm to 2 mm. The thickness of the cover may vary along the longitudinal axis. The thickness of the cover, such as a cover part in a center section (0.25 L to 0.75 L) of the oral drug delivery device along the longitudinal axis, may be in the range from 0.05 to 0.2 mm, such as from 0.06 mm to 0.15 mm.

The cover may be a two-part cover, e.g. with partly overlapping first cover part and second cover part. The first cover part may form the first end of the oral drug delivery device, and the second cover part may form the second end of the oral drug delivery device.

The actuator mechanism is engaged with the first attachment part/drug delivery member and/or the body. The actuator mechanism is configured to rotate the first attachment part/drug delivery member about a first rotation axis, e.g. in relation to the body. The first rotation axis may form an angle larger than 45 degrees, e.g. larger than 60 degrees, with the longitudinal axis. In one or more examples, the first rotation axis is perpendicular to the longitudinal axis or forms an angle of 90±10 degrees with the longitudinal axis. The actuator mechanism may comprise a first actuator and optionally a second actuator.

The drug delivery device may comprise a first attachment part having a first distal end and configured to deliver an active drug substance.

The drug delivery device may comprise a drug delivery member having a first distal end and configured to deliver an active drug substance.

The first attachment part may comprise a base and a needle part. The needle part optionally forms the first distal end and may be fixed to or integrated with the base. The base may be ring-shaped with the needle part extending from the outer surface of the base. The base may comprise a hinge cavity. The hinge cavity of the base may accommodate at least a part of a shaft or rod and optionally a part of the actuator mechanism, such as the first actuator.

The drug delivery member may comprise a base and/or a needle part. The needle part optionally forms the first distal end and may be fixed to or integrated with the base.

The first attachment part may be seen as any kind of attachment part that may be capable of attaching the oral drug delivery device to a biological tissue, such as a stomach wall, a wall of the bowels and/or intestines of a human or animal body. The first attachment part may be configured to attach the drug delivery device to a patient. The first attachment part may be configured to deliver an active drug substance. The oral drug delivery part may have only a single attachment part/drug delivery member.

The first attachment part can be connected within the body, such as via a shaft of the body/first body part. The first attachment part may be translatable attached with respect to the body. The first attachment part may be configured to move with respect to the body. For example, the first attachment part may be rotationally attached within the body, such as via the base of the first attachment part. The first attachment part can be configured, via the actuator mechanism, to transition from an initial position to a first position also denoted attached position. In the initial position, the first attachment part or at least parts or sections thereof may be located within the body. For example, a first distal end and/or a distal section of the first attachment part may be located within the body in the initial position. The first distal end can exit or "clear" the body when transitioning, such as rotating from the initial position to the first position. In other words, the first attachment part, such as the first distal end and/or distal section, may be configured to rotate external to the body. For example, the first distal end may be external to the body at least during a 100 degree rotation of the first attachment part.

The drug delivery member can be connected within the body. The drug delivery member may be translatable attached with respect to the body. The drug delivery member may be configured to move with respect to the body. For example, the drug delivery member may be rotationally attached within the body, such as via the base of the drug delivery member. The drug delivery member can be configured, via the actuator mechanism, to transition from an initial position to a first position also denoted attached position. In the initial position, the drug delivery member or at least parts or sections thereof may be located within the body. For example, a first distal end and/or a distal section of the drug delivery member may be located within the body in the initial position. The first distal end can exit or "clear" the body when transitioning, such as rotating from the initial position to the first position. In other words, the drug delivery member, such as the first distal end and/or distal section, may be configured to rotate external to the body. For example, the drug delivery member may be external to the body at least during a 100 degree rotation of the drug delivery member.

In one or more examples, the needle part has a first spike arranged at the first distal end, the first spike configured to penetrate biological tissue, such as a surface of a gastrointestinal tract. The first spike optionally forms a sharp tip to allow the needle part to penetrate tissue, e.g. during rotation from the initial position to the first position.

In one or more examples, the needle part has a proximal section and/or a distal section optionally with a bend therebetween. The bend may have a bending angle in the range from 60 degrees to 135 degrees, such as 90±10 degrees.

The needle part, such as the proximal section and/or the distal section, may be made of a material comprising one or more polymers, such as a biodegradeable polymer. In one or more examples, the needle part, such as the proximal section and/or the distal section, may comprise one or more polymers, such as polyethylene glycol (PEG), polyethylene oxide (PEO), poly(oxyethylene) (POE), and polylactic acid (PLA).

The needle part, such as the proximal section and/or the distal section, may be made of a biodissolvable material.

The first attachment part/drug delivery member, such as the distal section and/or the proximal section, may comprise a drug cavity configured to accommodate the active drug substance. In one or more examples, an active drug substance is embedded or integrated in a bio-degradable part of the first attachment part/drug delivery member, such as the (distal section of) needle part. In other words, the needle part, such as one or more, such as all of the proximal section, the distal section, and the bend, may comprise an active drug substance embedded in the needle part, such as embedded in a polymer material of the needle part.

In one or more example drug delivery devices, the oral drug delivery device may be configured with detachment capabilities. For example, the oral drug delivery device may be constructed in a way that releases the oral drug delivery device or at least parts thereof from internal tissues and/or internal surfaces, such as after distribution of the active drug substance. Accordingly, a biodegradeable needle part, such as distal section, may facilitate or provide such detachment capability.

The needle part, such as the proximal section and/or the distal section, may be made of a metal or a metal alloy.

The needle part or first spike may have a length in the range from 1 mm to 15 mm, such as in the range from 3 mm to 10 mm. Thereby sufficient penetration into the internal tissue may be provided for while at the same time reducing the risk of damaging the internal tissue. The first distal end of the first attachment part may be provided with a gripping part configured to grip a biological tissue.

The needle part may be straight and/or curved. The first attachment part/drug delivery member may include one, two, or more straight portions or sections formed at an angle, thereby forming the bend therebetween. The bend can separate the proximal section from the distal section, such as connecting the proximal section to the distal section. In one or more example oral drug delivery devices, the distal section extends at an angle between 30 to 80 degrees or at an angle between 100-170 degrees from the longitudinal axis in the first position. In other words, the distal section may, in the first position of the first attachment part, form an angle in the range from 30 degrees to 80 degrees with the longitudinal axis.

The first attachment part, such as the distal section, can be held within the body, e.g. in the initial position of the first attachment part. The first attachment part can be rotatably connected to the body, such as to the first body part. In an initial configuration, the first attachment part/drug delivery member or parts thereof, such as the distal section, can be held fully within the body. This can be known as the initial position of the first attachment part/drug delivery member. In an attached configuration, the first attachment part/drug delivery member (in the first position) may at least partially extend outside the body. Thus, a first distal end and/or distal section of the first attachment part/drug delivery member can translate, such as rotate, from within the body, such as in the initial position of the first attachment part/drug delivery member, to outside of the body, such as the first position of the first attachment part/drug delivery member. This movement can occur during operation of the actuator mechanism.

The actuator mechanism may comprise a first actuator, such as a first spring. The first spring may be a spiral spring, such as a torsion spring, a blade spring, such as a coiled blade spring, or an elastic member. The first actuator may be made of a metal or a metal alloy. The first actuator may be made of an elastic polymer material. The first actuator may have a first end part engaged with or configured to engage with the body, such as with a shaft or rod of the first body part. The first actuator may have a second end part engaged with or configured to engage with the first attachment part, such as a hinge cavity in a base of the first attachment part. The first actuator may be configured to rotate the first attachment part about the first rotation axis in relation to the body. The first actuator may be configured to, e.g. via the base of the first attachment part, break or weaken the cover. The first actuator may be configured to, e.g. via a rotation of the base of the first attachment part, move the second body part in relation to the first body part and thereby configured to break or weaken the cover.

In one or more examples, the first actuator comprises a spiral spring, such as a torsion spring, a blade spring, such as a coiled blade spring, or an elastic member having a first end or first end part engaging with the first body part, e.g. a shaft of the first body part. The first actuator may be arranged in a hinge cavity of the base of the first attachment part. The first actuator may have a second end or second end part engaging with the first attachment part, such as with a recess in hinge cavity.

The actuator mechanism may comprise a second actuator, such as a second spring. The second spring may be a spiral spring, such as a torsion spring, a blade spring, such as a coiled blade spring, or an elastic member. The second actuator may be made of a metal or a metal alloy. The second actuator may be made of an elastic polymer material. The second actuator may be configured to break or weaken the cover. The second actuator have a first end engaged with or configured to engage with a first body part of the body or a second secondary body part of a second body part. The second actuator may have a second end engaged with or configured to engage with a second body part of the body. The second actuator may be configured to move the second body part, such as a second primary body part, in relation to the first body part and thereby configured to break or weaken the cover.

In one or more examples, the actuator mechanism comprises a first actuator and/or a second actuator, the first actuator configured to rotate the first attachment part/drug delivery member about a first rotation axis, and the second actuator configured to break or weaken the cover.

The oral drug delivery device comprises a body. The body housing includes a first body end and a second body end. The first body end is opposite the second body end. In one or more oral drug delivery devices, the body, such as one or more locking elements of the body or body part(s) of the body, can be configured to retain certain components of the oral drug delivery device in an initial position. For example, the body can retain one or more of the first attachment part and the actuator mechanism. The body can form a first cavity and/or a second cavity as discussed herein. The body can be configured to at least partially contain (e.g., surround) components of the oral drug delivery device. For example, the body can at least partially accommodate the actuator mechanism. The body can at least partially accommodate the first attachment part.

In one or more oral drug delivery devices, the body may be a one-part or single-part body, e.g., unitary. In one or more oral drug delivery devices, the body can be made up of one or more body parts, such as first body part, a second body part and optionally a third body part. The body includes an outer surface.

In one or more examples, the body comprises a first body part and a second body part. The actuator mechanism is optionally configured to move the second body part in relation to the first body part, e.g. to break or weaken the cover prior to or during rotation of the first attachment part.

The first body part may form a first side wall of the body. In other words, the first body part may comprise a first side element. The first body may form an end wall or end part of the body.

The second body part may form a second side wall of the body. In other words, the second body part may comprise a second side element. The first body may form an end wall or end part of the body. The second body part may be configured as a stop member for the first distal end of the first attachment part.

The first attachment part/drug delivery member, such as the base and/or the needle part may in the initial position of the first attachment part extend between the first side wall and the second side wall of the body.

The body may comprise a third body part. The third body part may be made of a biodegradeable material. The third body part may be configured as a stop member for the first distal end of the first attachment part.

In one or more examples, the actuator mechanism is configured to move the second body part in relation to the first body part by moving the second body part in relation to, e.g. outward and/or away from, the first body part along the first rotation axis.

In one or more examples, the actuator mechanism is configured to rotate the second body part in relation to the first body part about an actuation axis, the actuation axis forming an angle with the first rotation axis larger than 45 degrees. The actuation axis may be perpendicular to or form an angle of 90±10 degrees with the longitudinal axis and/or with the first rotation axis.

In one or more examples, the first rotation axis is arranged between the first end and a center of the oral drug delivery device along the longitudinal axis, and the actuation axis is arranged between the center and the second end of the oral drug delivery device.

In one or more examples, the first rotation axis is arranged at a first distance in the range from 0.4 L to 0.6 L from the first end, such as at a center of the oral drug delivery device, along the longitudinal axis, and the first rotation axis is optionally perpendicular to the longitudinal axis, wherein L is the length of the oral drug delivery device. A centered first rotation axis allows for less rotation, e.g. less than 180 degrees, for attachment to the gastrointestinal tract thereby reducing the rotational length requirements for the first actuator. Further, a more space-efficient oral drug delivery device is allowed for, e.g. by simplifying the actuator mechanism.

In one or more example oral drug delivery devices, the first rotation axis is arranged closer to the first end than the second end. In one or more example oral drug delivery devices, the first rotation axis is arranged between the first end and a center along the longitudinal axis. In one or more example oral drug delivery devices, the first rotation axis is arranged closer to the first end than a center of the body. For example, the body can be defined as having a length L. The first rotation axis can be arranged at less than 0.4 L, such as less than 0.25 L from the first end of the body. The first rotation axis can be arranged at 0.1 L, 0.2 L, 0.3 L, 0.4 L from the first end of the body. A first rotation axis near the first end may allow for a larger rotation angle which may increase the chance of the first attachment part/distal end engaging with tissue during the rotation thereof outside the housing. The first rotation axis can be arranged at larger than 0.6 L, such as larger than 0.75 L from the second end of the housing.

In one or more example oral drug delivery devices, the first attachment part/drug delivery member, such as the first distal end can rotate out of the body. In one or more example oral drug delivery devices, the first attachment part/drug delivery member, such as the distal end/distal section, can rotate (partially and/or fully) into the body, e.g. after being rotated out of the body.

In one or more examples, the actuator mechanism is configured to move the second body part in relation to the first body part by moving the second body part, e.g. at least 1 mm, in relation to the first body part along the longitudinal axis.

In one or more examples, rotation of the first attachment part/drug delivery member is triggered by a movement of the second body part from an initial position to a first position in relation to the first body part.

In one or more examples, the first body part comprises a shaft, the first attachment part comprising a base and a needle part, wherein the shaft is arranged in a hinge cavity of the base.

In one or more examples, the actuation axis is perpendicular to the longitudinal axis.

In one or more examples, the first attachment part/drug delivery member is configured to rotate more than 120 degrees, such as in the range from 135 degrees to 180 degrees, from an initial position to a first position about the first rotation axis. For example, the first attachment part/drug delivery member may be configured to rotate 160±10 degrees from an initial position to a first position about the first rotation axis. In one or more examples, the first attachment part/drug delivery member is configured to rotate more than 270 degrees, such as in the range from 280 degrees to 350 degrees, from an initial position to a first position about the first rotation axis.

The oral drug delivery device optionally comprises a stop member for controlling rotation of the first attachment part about the first rotation axis. The stop member may be configured as a rotational stop for the first attachment part. In other words, the stop member may limit rotation of the first attachment part to a maximum rotation angle, e.g. in the range from 180 degrees to 350 degrees or in the range from 135 degrees to 180 degrees. The stop member may comprise a stop part configured to engage with corresponding stop part on base of the first attachment part to stop rotation of the first attachment part in a first position of the first attachment part in relation to the body. The stop member may be glued or otherwise fixed to the shaft.

Figure 1B:
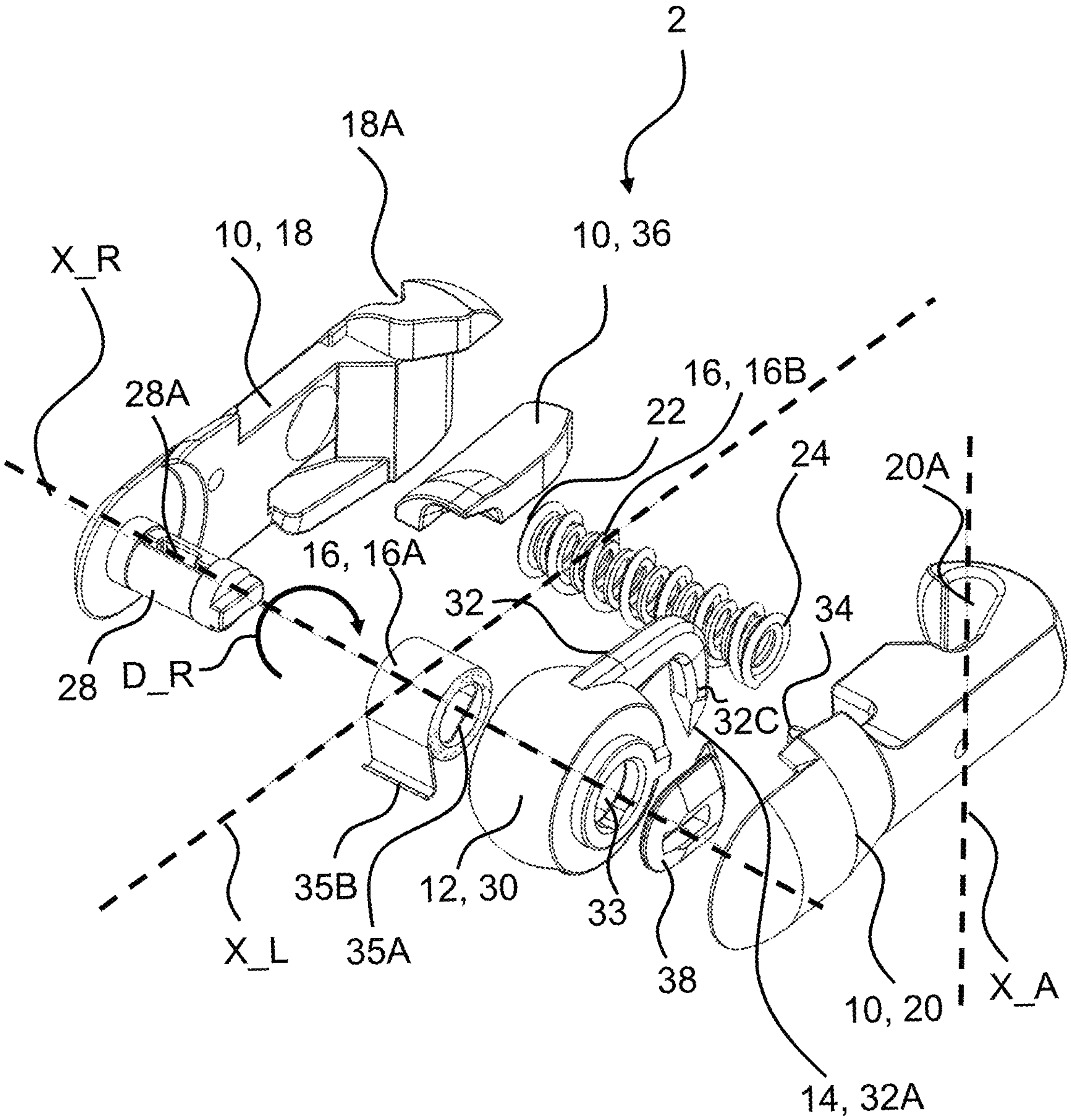

FIGS. 1A-1E show different views of an example oral drug delivery device. FIG. 1A shows an exploded view of oral drug delivery device 2 comprising a cover 4 including a first cover part 4A and a second cover part 4B and FIG. 1B shows an exploded view of oral drug delivery device 2 without cover. The oral drug delivery device 2 has or defines a longitudinal axis X_L and extends from a first end 6 to a second end 8. The oral drug delivery device 2 comprises a body 10; a first attachment part 12 having a first distal end 14 and configured to deliver an active drug substance; and an actuator mechanism 16 engaged with the first attachment part 12 and configured to rotate the first attachment part 12, e.g. at least 180 degrees, such as at least 270 degrees, about a first rotation axis X_R perpendicular to the longitudinal axis X_L and thus forming an angle larger than 45 degrees with the longitudinal axis X_L. The oral drug delivery device 2 is configured to break or weaken the cover 4, such as first cover part 4A and/or second cover part 4B, prior to or during rotation of the first attachment part 12.

The actuator mechanism 16 comprises a first actuator 16A and a second actuator 16B. The first actuator 16A is a coiled blade spring and is configured to rotate the first attachment part 12 about the first rotation axis X_R. The second actuator 16B is a coil spring and is configured to break or weaken the cover 4, such as first cover part 4A and/or second cover part 4B.

The body 10 comprises a first body part 18 and a second body part 20, and the actuator mechanism 16/second actuator 16B is configured to move the second body part 20 in relation to the first body part 18 to break or weaken the cover 4 prior to or during rotation of the first attachment part 12.

The second actuator 16B has a first end 22 and a second end 24, the first end 22 engaging the first body part 18 and the second end 24 engaging the second body part 20. Thereby, the actuator mechanism 16/second actuator 16B is configured to move the second body part 20 in relation to the first body part by moving the second body part 20 in relation to the first body part 18 along the first rotation axis X_R.

The first body part 18 and the second body part 20 optionally comprises respective first joint part 18A and second joint part 20A forming an actuation joint 26 with an actuation axis X_A. The actuator mechanism 16/second actuator 16B is configured to rotate the second body part 20 in relation to the first body part 18 about the actuation axis X_A. The actuation axis X_A may be perpendicular to the longitudinal axis X_L and/or perpendicular to the first rotation axis X_R. The first rotation axis X_R is arranged between the first end 6 and a center C of the oral drug delivery device 2 along the longitudinal axis X_R, and the actuation axis X_A is arranged between the center C and the second end 8 along the longitudinal axis X_R.

The first body part 18 comprises a shaft 28 configured to engage with the first attachment part 12, the first attachment part 12 comprising a base 30 and a needle part 32, wherein the shaft 28 is arranged in a hinge cavity 33 of the base 30. The shaft 28 optionally engages with a first end part 35A of the first actuator 16A, and the base 30 engages with a second end part 35B of the first actuator 16A.

The needle part 32 has a first spike 32A arranged at the first distal end 14, the first spike 32A configured to penetrate a surface of a gastrointestinal tract. Further, the needle part 32 has a proximal section 32B and a distal section 32C with a bend 32D therebetween, the bend having a bending angle in the range from 60 degrees to 135 degrees.

The second body part 20 optionally comprises a locking element 34 configured to engage the first attachment part 12, such as the needle part 32, and lock, in the initial position of the second body part, the first attachment part 12, i.e. prevent rotation of the first attachment part 12 about the first rotation axis X_R, e.g. at least in one direction.

The body 10 is a multi-part body and optionally comprises a third body part 36.

The oral drug delivery device 2 optionally comprises a stop member 38 for controlling rotation of the first attachment part about the first rotation axis. The stop member 38 may be configured as a rotational stop for the first attachment part 12. In other words, the stop member 38 may limit rotation of the first attachment part 12 to a maximum rotation angle, e.g. in the range from 180 degrees to 350 degrees. The stop member 38 comprises stop part 38A configured to engage with corresponding stop part 30B on base part 30 of the first attachment part to stop rotation of the first attachment part 12 in a first position of the first attachment part 12 in relation to the body 10. The stop member 38 may be glued or otherwise fixed to the shaft 28.

Figure 1C:
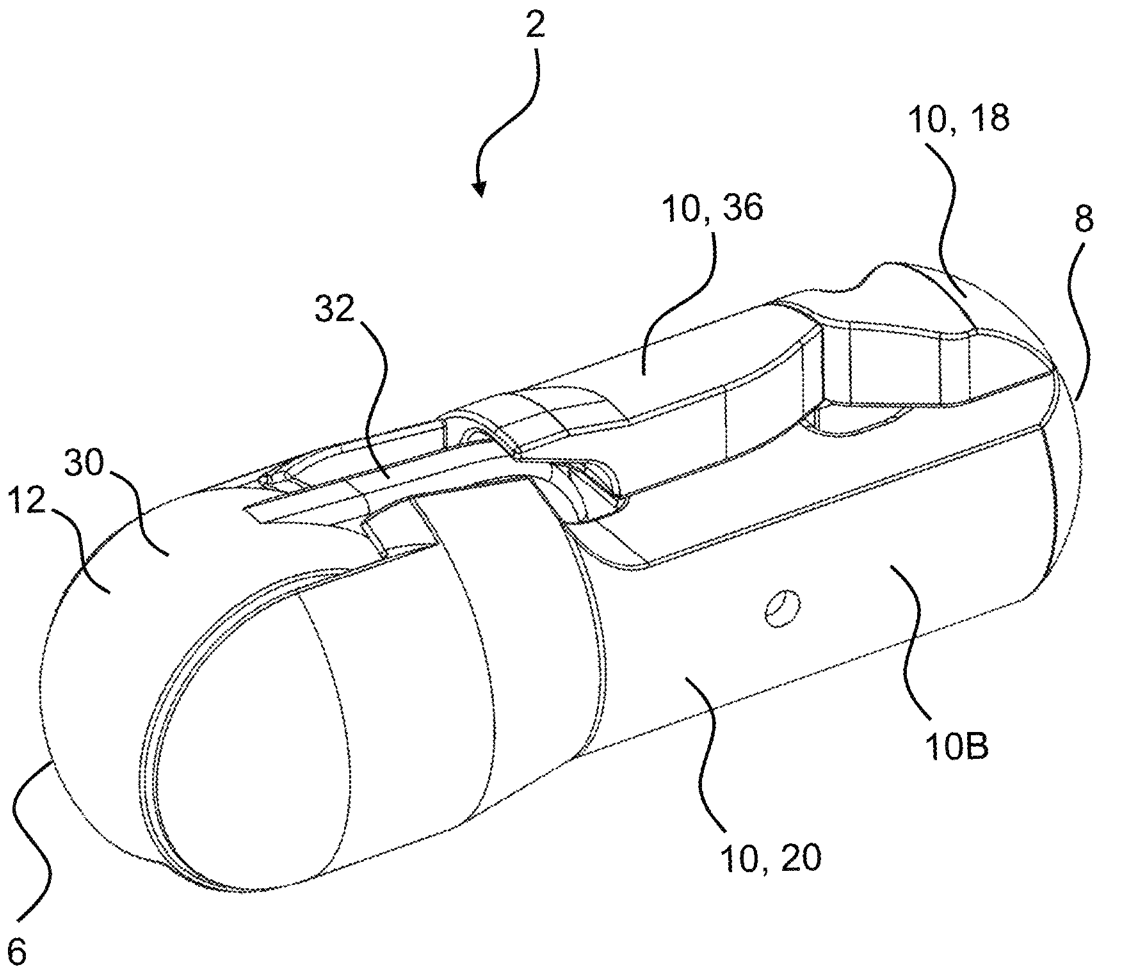
Figure 1D:
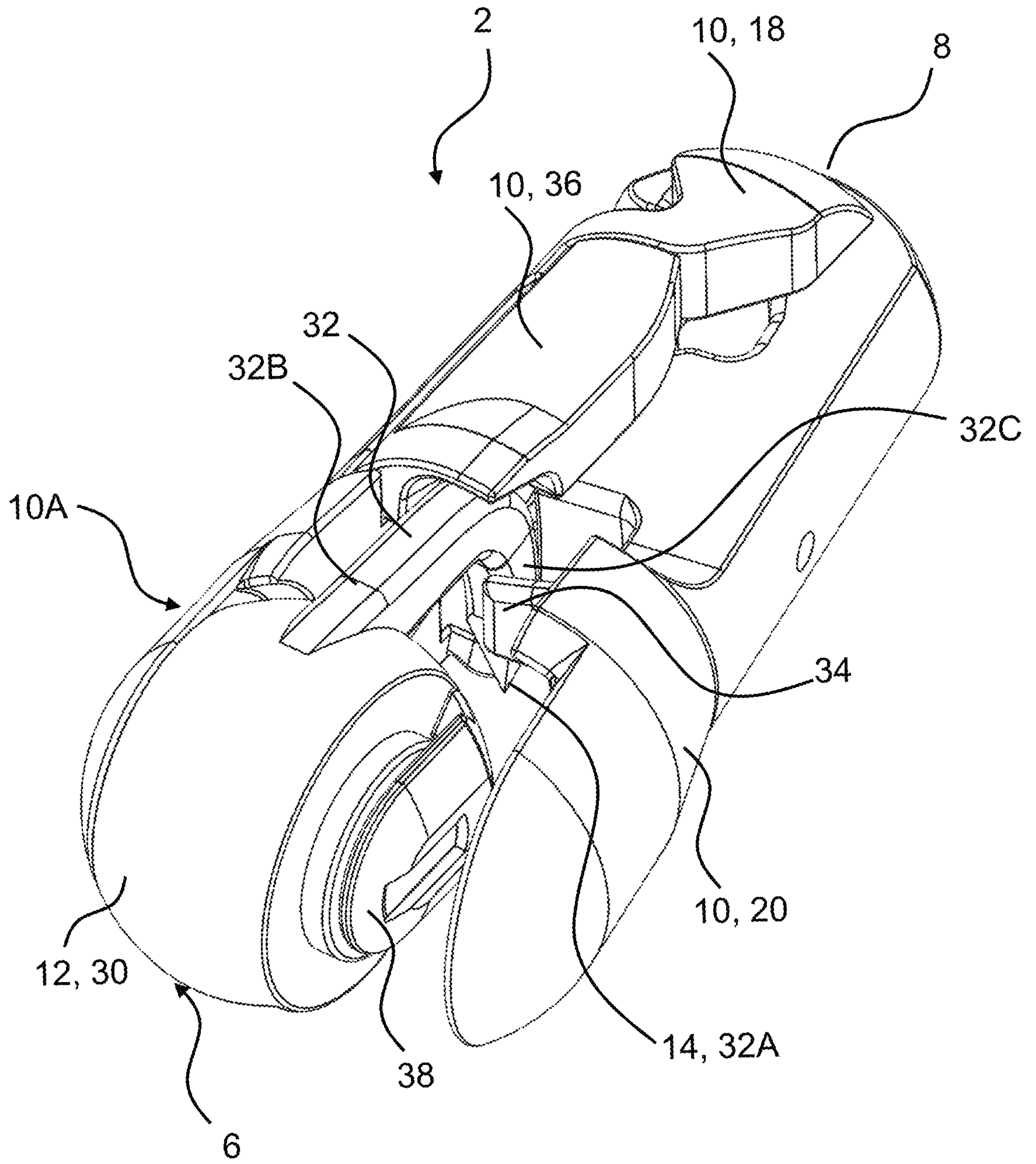

FIGS. 1C and 1D show perspective views of the oral drug delivery device 2 without cover 4. In FIG. 1B, the second body part 20 is in an initial position and kept in the initial position by cover 4. In the initial position, the locking element 34 of the second body part 20 engages with the first attachment part and prevents rotation of the first attachment part 12 about the first rotation axis X_R. The second actuator 16B applies pressure to the second body part 20 thereby weakening or breaking the cover 4 such that the second body 20 rotates about the actuation axis X_A to move the second body part 20 to a first position shown in FIG. 1C in relation to the first body part 18 along the first rotation axis X_R. The movement from the initial position to the first position, results in the locking element 34 disengaging with the first attachment part 12, whereby the first actuator 16A rotates the first attachment part 12 about the rotation axis, e.g. more than 100 degrees, such as in the range from 180 degrees to 350 degrees.

The first body part 18 forms a first side wall 10A of the body, and the second body part 20 forms a second side wall 10B of the body 10 with the first attachment part 12 in the initial position extending between the first side wall 10A and the second side wall 10B of the body. The second body part 20 forms an end part 10C.

In the oral drug delivery device 2, rotation of the first attachment part 12 is optionally triggered by a movement of the second body part 20 from an initial position shown in FIG. 1B to a first position shown in FIG. 1C in relation to the first body part 18. The first attachment part 12 is configured to rotate more than 120 degrees from an initial position as in FIGS. 1A-1D to a first position about the first rotation axis X_R in the direction indicated by arrow D_R.

Figure 1E:
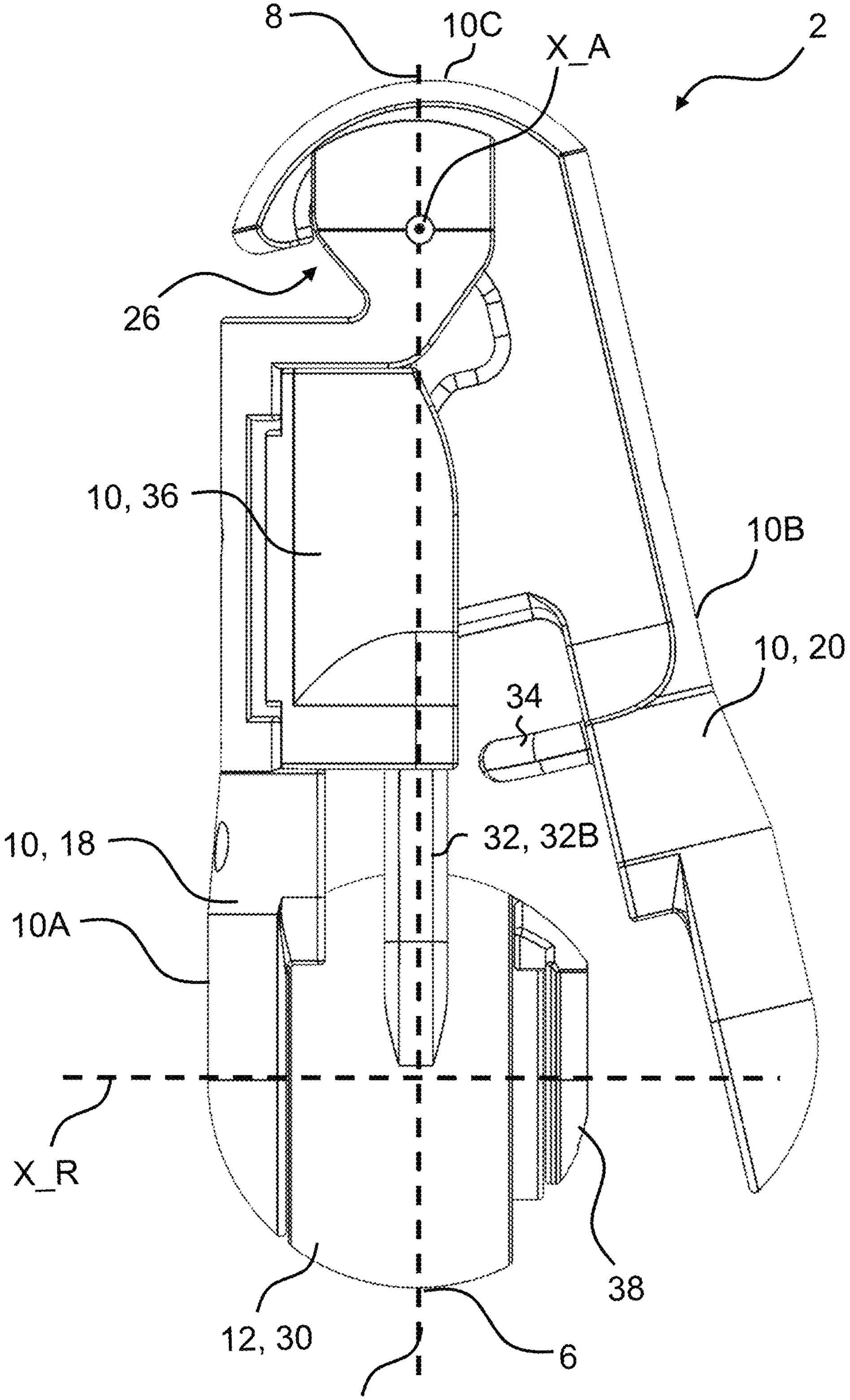

FIG. 1E shows a first view of the oral drug delivery device 2 without cover 4. The second body part 20 has been rotated about the actuation axis X_A thereby breaking or weakening the cover due to force from the second actuator. Further, the locking element 34 has disengaged from the first attachment part 12 thereby allowing the first attachment part 12 to rotate about the rotation axis X_R due to rotational force from the first actuator. The three axes X_R, X_L, and X_A are orthogonal, however variations such as +30 degrees between the axes may be implemented.

For the sake of illustration, the first attachment part 12 in FIG. 1A is shown with a needle part 32 formed from a metal or metal alloy, where the distal section 32C comprises a drug cavity 46 for accommodating an active drug substance. In FIGS. 1B to 1E, the first attachment part 12 is shown with a needle part 32 made from a biodegradeable and biodissolve polymer, where an active drug substance is accommodated in a drug cavity of the proximal section, distal section and/or bend (not shown) and/or embedded in the biodegradeable and biodissolve polymer.

Figure 2A:
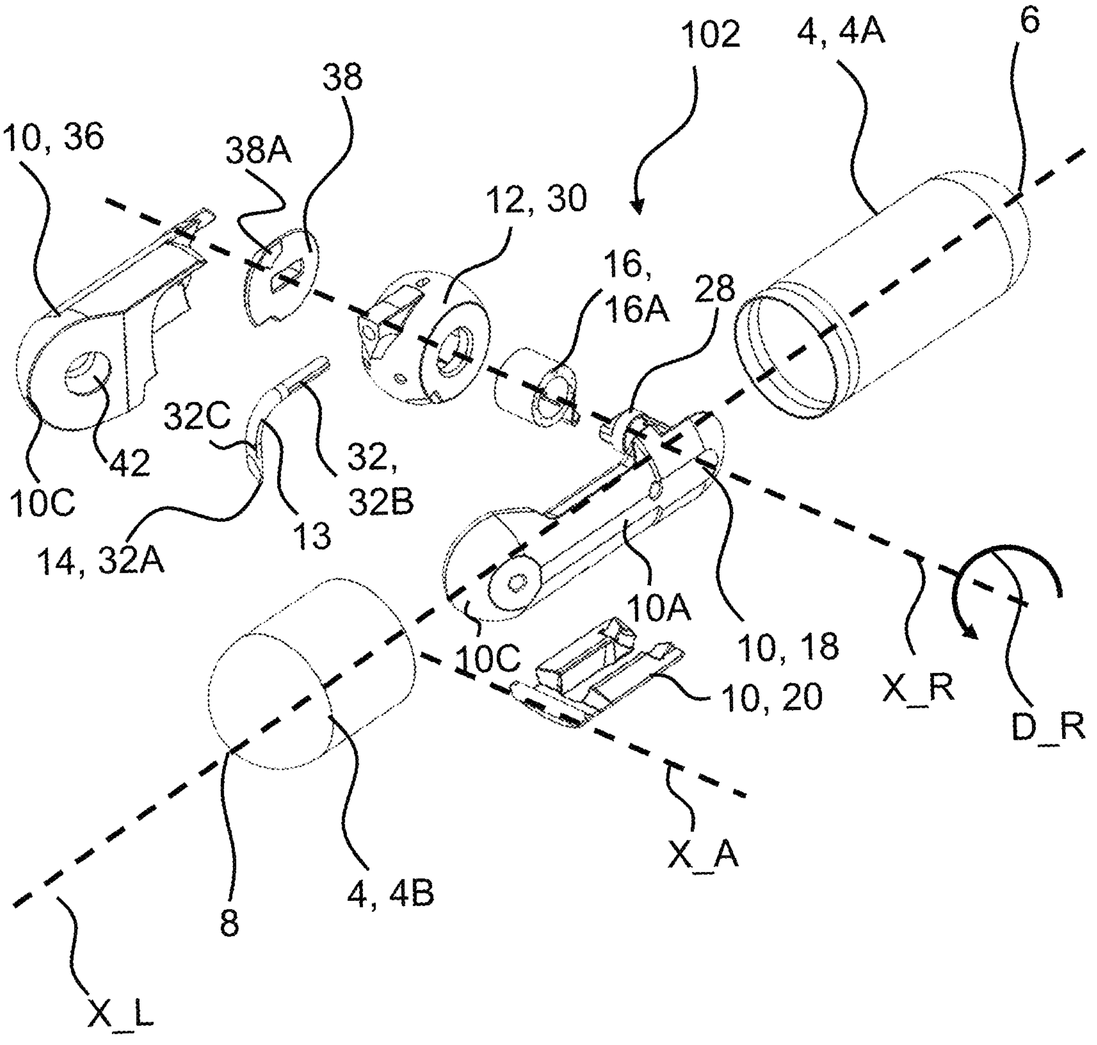
FIGS. 2A-2E show different views of an example oral drug delivery device.
Figure 2B:
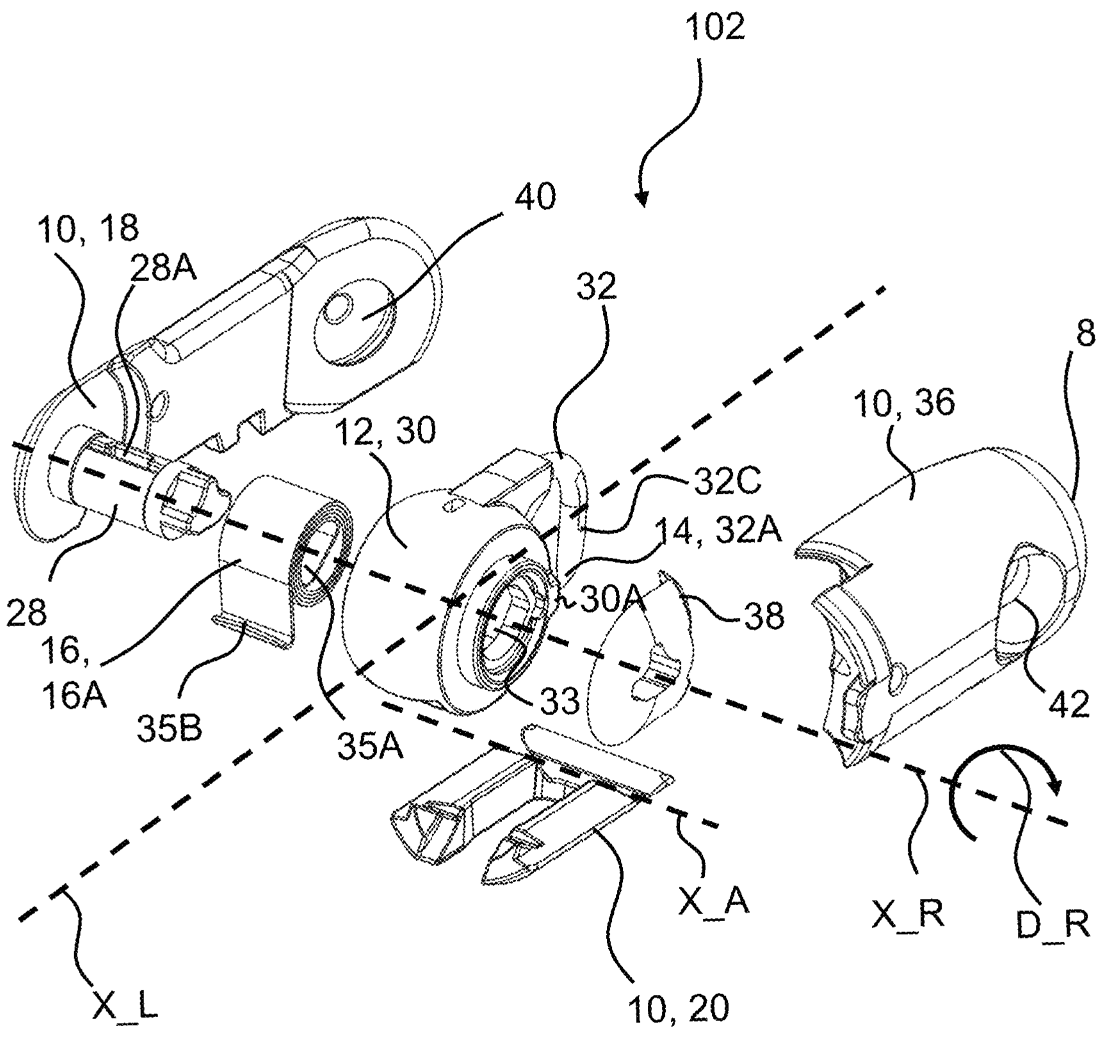

FIGS. 2A-2E show different views of an example oral drug delivery device. FIG. 2A shows an exploded view of oral drug delivery device 102 comprising a cover 4 including a first cover part 4A and a second cover part 4B and FIG. 2B shows an exploded view of oral drug delivery device 102 without cover. The oral drug delivery device 102 has or defines a longitudinal axis X_L and extends from a first end 6 to a second end 8. The oral drug delivery device 102 comprises a body 10; a first attachment part 12 having a first distal end 14 and configured to deliver an active drug substance; and an actuator mechanism 16 engaged with the first attachment part 12 and configured to rotate the first attachment part 12, e.g. at least 180 degrees, such as at least 270 degrees, about a first rotation axis X_R perpendicular to the longitudinal axis X_L and thus forming an angle larger than 45 degrees with the longitudinal axis X_L. The oral drug delivery device 102 is configured to break or weaken the cover 4, such as first cover part 4A and/or second cover part 4B, prior to or during rotation of the first attachment part 12.

The actuator mechanism 16 comprises a first actuator 16A. The first actuator 16A is a coiled blade spring and is configured to rotate the first attachment part 12 about the first rotation axis X_R and thereby configured to break or weaken the cover 4, such as first cover part 4A and/or second cover part 4B.

The body 10 comprises a first body part 18 and a second body part 20, and the actuator mechanism 16/first actuator 16A is configured via the base 30 of the first attachment part 12 to move the second body part 20 in relation to the first body part 18 to break or weaken the cover 4 prior to or during rotation of the first attachment part 12.

The actuator mechanism 16/first actuator 16A is configured to rotate the second body part 20 in relation to the first body part 18 about the actuation axis X_A via the base 30. The actuation axis X_A is parallel to the first rotation axis X_R. The first rotation axis X_R is arranged between the first end 6 and a center C of the oral drug delivery device 102 along the longitudinal axis X_R.

The first body part 18 comprises a shaft 28 configured to engage with the first attachment part 12, the first attachment part 12 comprising a base 30 and a needle part 32, wherein the shaft 28 is arranged in a hinge cavity 33 of the base 30. The shaft 28 optionally engages with a first end part 35A of the first actuator 16A, and the base 30 engages with a second end part 35B of the first actuator 16A.

The needle part 32 has a first spike 32A arranged at the first distal end 14, the first spike 32A configured to penetrate a surface of a gastrointestinal tract. Further, the needle part 32 has a proximal section 32B and a distal section 32C with a bend 32D therebetween, the bend 32D having a bending angle in the range from 60 degrees to 135 degrees, such as 90 degrees as illustrated.

The body 10 is a multi-part body and optionally comprises a third body part 36. The third body part 36 may be attached to the first body part 18 via a dissolvable plug (not shown) in recess 40 or through-going bore of the first body part 18 and in throughgoing bore 42 or recess of the third body part 36.

The oral drug delivery device 102 optionally comprises a stop member 38 for controlling rotation of the first attachment part 12 about the first rotation axis X_R. The stop member 38 may be configured as a rotational stop for the first attachment part 12. In other words, the stop member 38 may limit rotation of the first attachment part 12 to a maximum rotation angle, e.g. in the range from 180 degrees to 350 degrees. The stop member 38 comprises stop part 38A configured to engage with corresponding stop part 30B on base part 30 of the first attachment part to stop rotation of the first attachment part 12 in a first position of the first attachment part 12 in relation to the body 10. The stop member 38 may be glued or otherwise fixed to the shaft 28.

The first body part 18 forms a first side wall 10A of the body, and the third body part 36 forms a second side wall 10B of the body 10 with the first attachment part 12 in the initial position extending between the first side wall 10A and the second side wall 10B of the body. The first body part 18 and the third body part 36 forms an end part 10C of the body.

Figure 2C:
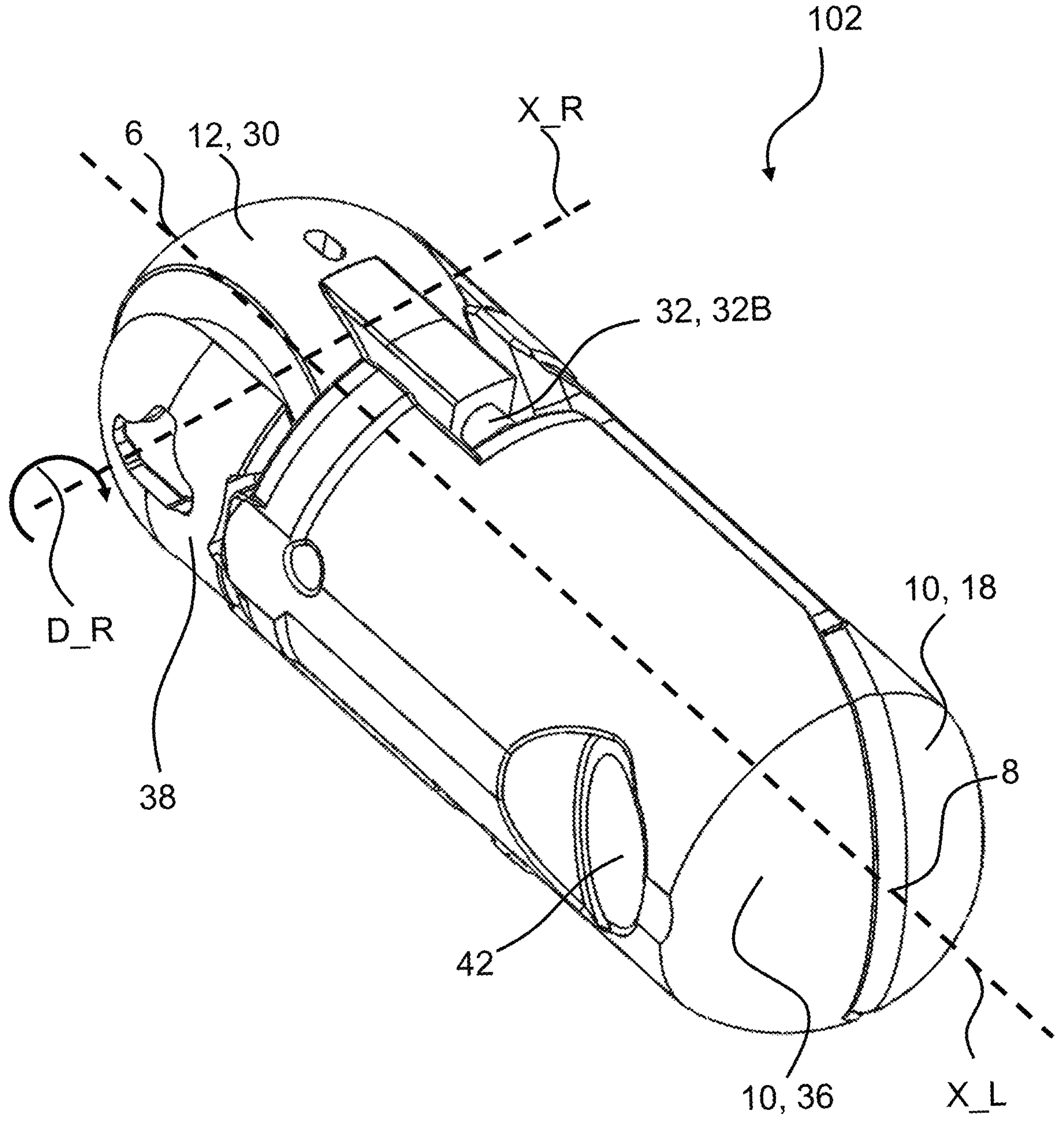
Figure 2D:
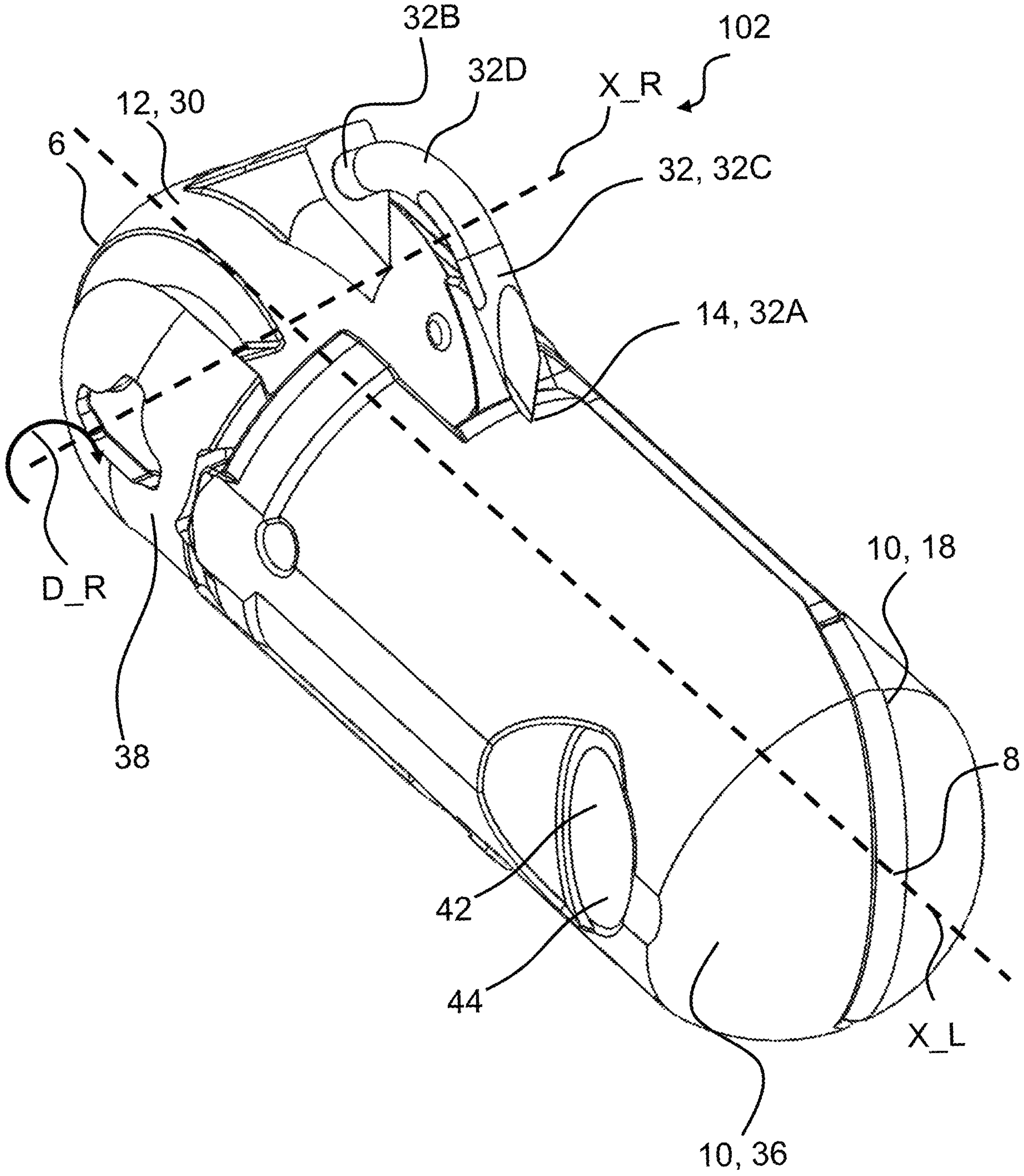

FIGS. 2C and 2D show perspective views of the oral drug delivery device 102 without cover 4. In FIG. 1B, the second body part 20 and the first attachment part 12 are in respective initial positions and kept in the initial position by cover 4. The first actuator 16A applies pressure to the second body part 20 via base 30 thereby weakening or breaking the cover 4 such that the second body 20 rotates along the actuation axis X_A to move the second body part 20 to a first position where the cover is weakened or broken. The movement from the initial position to the first position of the second body part 20 allows the first actuator 16A to further rotate the first attachment part 12 about the first rotation axis X_R, e.g. more than 100 degrees, such as in the range from 180 degrees to 350 degrees as illustrated in FIG. 2C, where the first rotation part 12 has been rotated about 270 degrees from the initial position.

In the oral drug delivery device 102, rotation of the first attachment part 12 is optionally triggered by a movement of the second body part 20 from an initial position to a first position in relation to the first body part 18. The first attachment part 12 is configured to rotate more than 120 degrees from an initial position as in FIG. 2B to a first position about the first rotation axis X_R in the direction indicated by arrow D_R as illustrated in FIG. 2C.

Figure 2E:
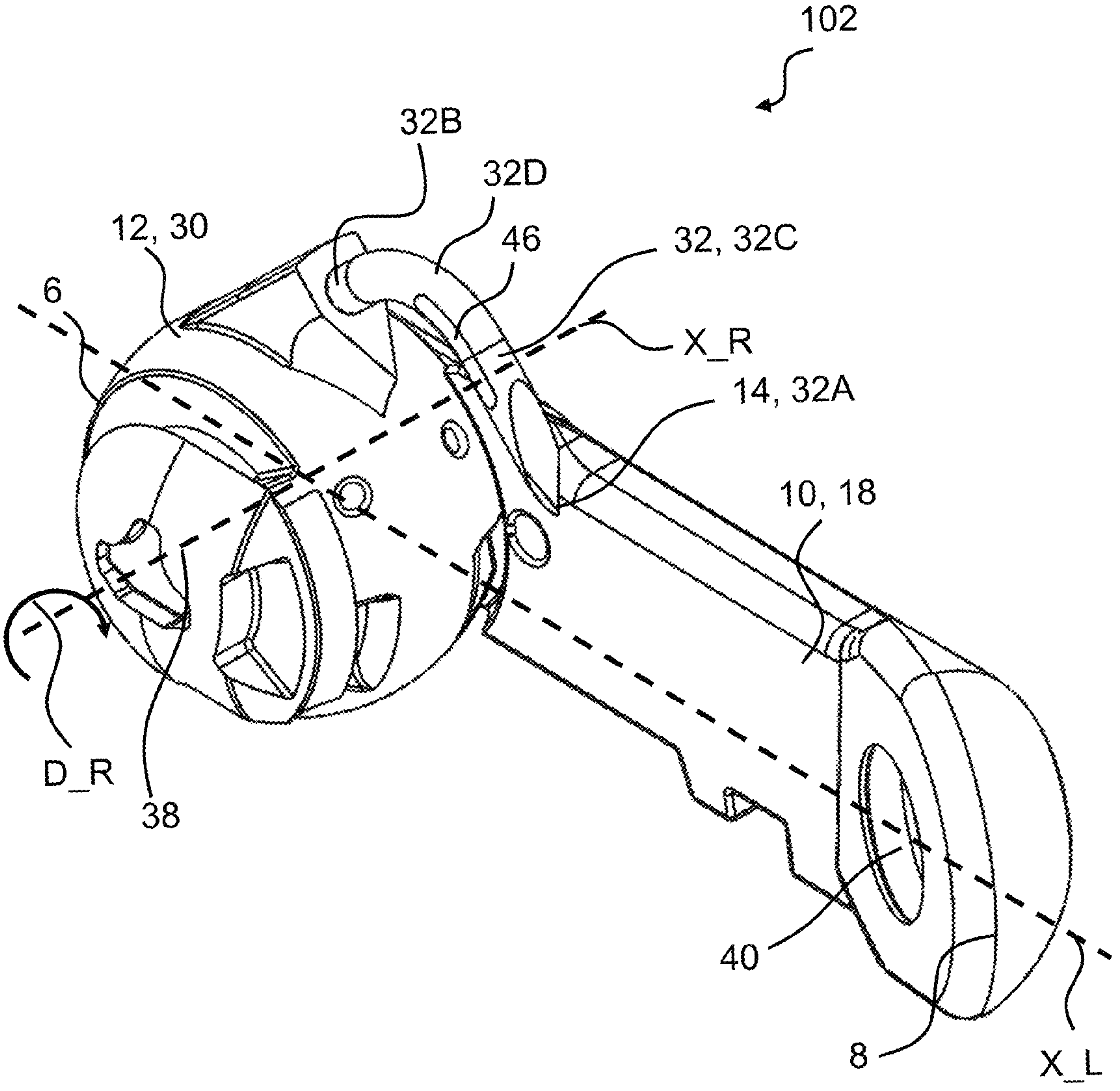

FIG. 2E shows a perspective view of the oral drug delivery device 102 without cover 4. The plug 44 has been dissolved from recess 40 and through-going bore 42 thereby releasing the third body part 36 (and the second body part 20) from the first body part 18. The second body part 20 has been rotated about the actuation axis X_A thereby breaking or weakening the cover 4 due to force from the first actuator 16A.

Figure 3A:
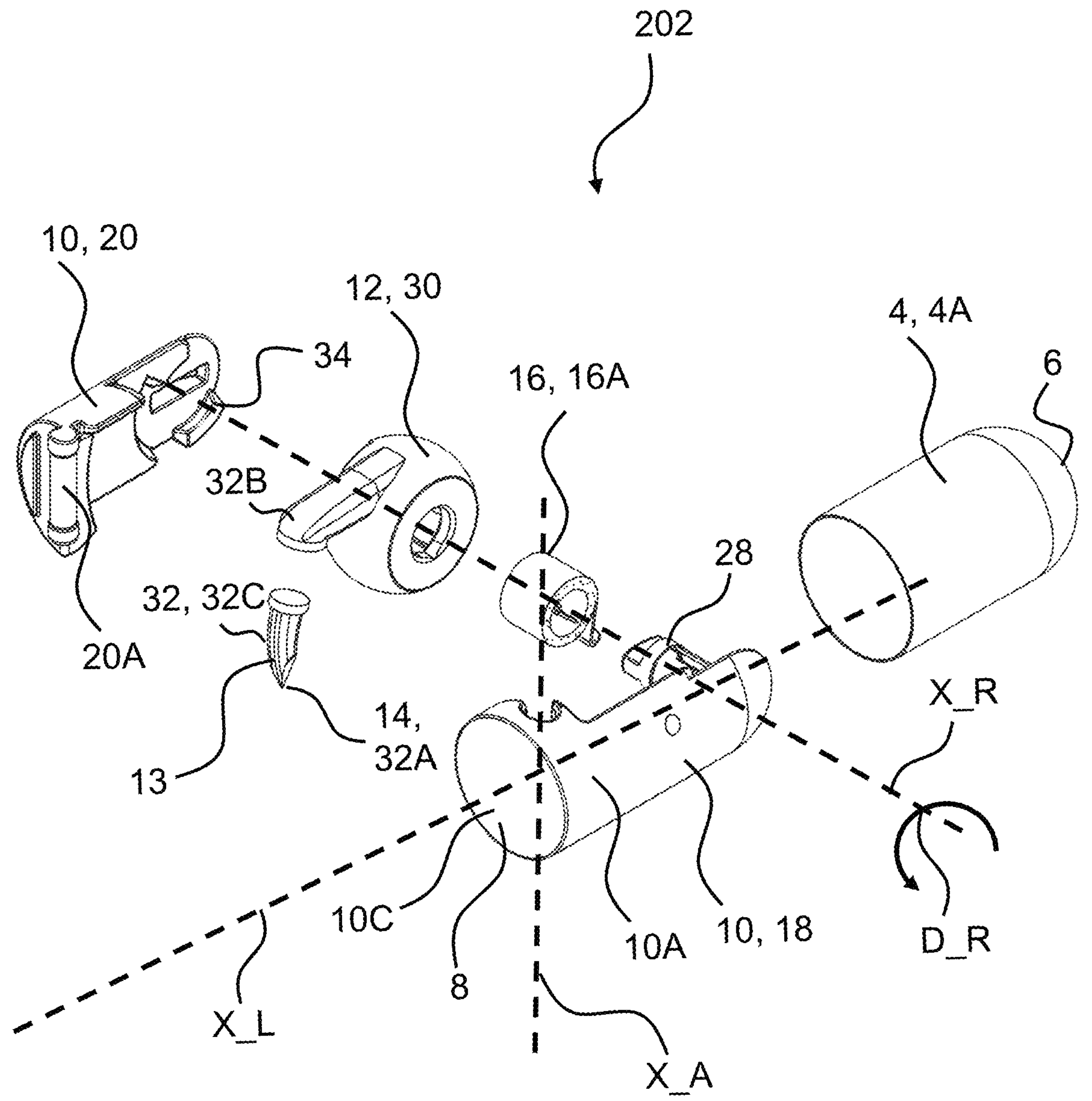
FIGS. 3A-3E show different views of an example oral drug delivery device.
Figure 3B:
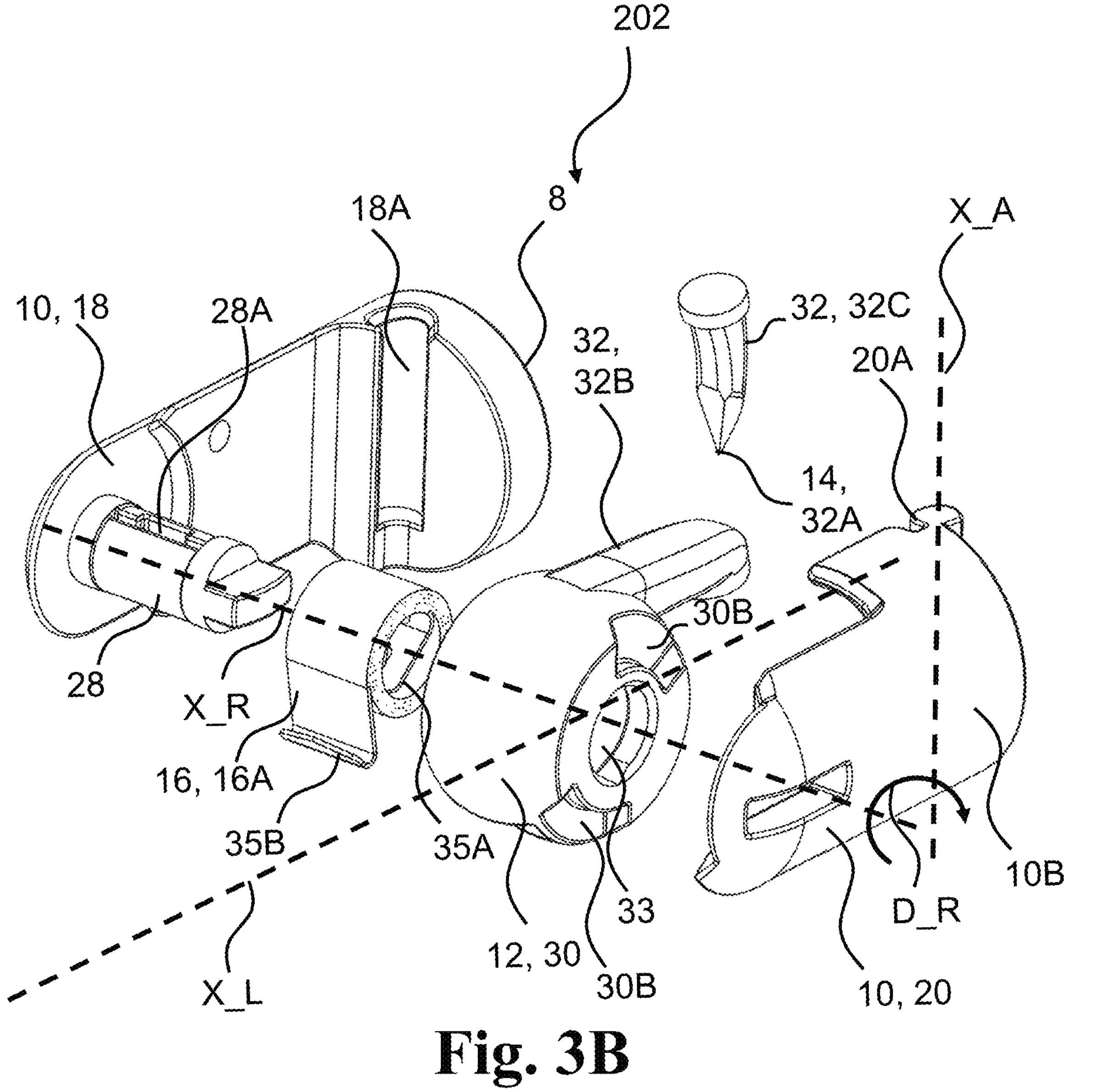
Figure 3C:
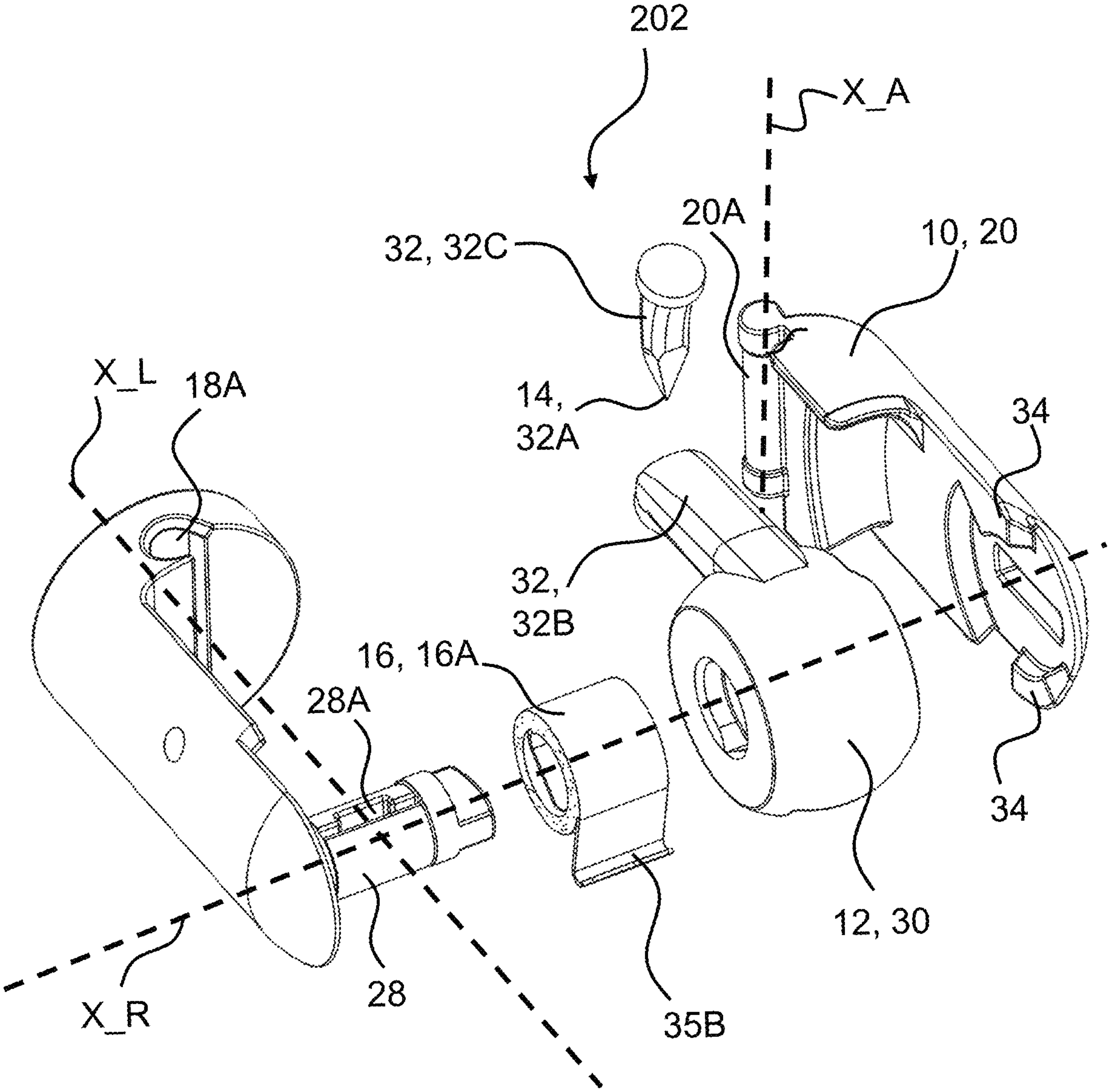

FIGS. 3A-3E show different views of an example oral drug delivery device. FIGS. 3A, 3B, and 3C show exploded views of oral drug delivery device 202 comprising a cover 4 including a first cover part 4A (not shown in FIGS. 3B and 3C). The oral drug delivery device 202 has or defines a longitudinal axis X_L and extends from a first end 6 to a second end 8. The oral drug delivery device 202 comprises a body 10; a first attachment part 12 having a first distal end 14 and configured to deliver an active drug substance; and an actuator mechanism 16 engaged with the first attachment part 12 and configured to rotate the first attachment part 12, e.g. at least 180 degrees, such as at least 270 degrees, about a first rotation axis X_R perpendicular to the longitudinal axis X_L and thus forming an angle larger than 45 degrees with the longitudinal axis X_L. The oral drug delivery device 202 is configured to break or weaken the cover 4, such as first cover part 4A and/or second cover part 4B, prior to or during rotation of the first attachment part 12.

The actuator mechanism 16 comprises a first actuator 16A. The first actuator 16A is a coiled blade spring and is configured to rotate the first attachment part 12 about the first rotation axis X_R and thereby configured to break or weaken the cover 4, such as first cover part 4A and/or second cover part 4B.

The body 10 comprises a first body part 18 and a second body part 20, and the actuator mechanism 16/first actuator 16A is configured via the base 30 of the first attachment part 12 to move the second body part 20 in relation to the first body part 18 as also described in FIGS. 1A-1D to break or weaken the cover 4 prior to or during rotation of the first attachment part 12. The base 30 is configured to contact and move the second body part 20 along the first rotation axis X_R when the first attachment part 12 is rotated about the first rotation axis.

The first body part 18 and the second body part 20 optionally comprises respective first joint part 18A and second joint part 20A forming an actuation joint 26 with an actuation axis X_A. The actuator mechanism 16/first actuator 16A is configured to rotate the second body part 20 in relation to the first body part 18 about the actuation axis X_A. The actuation axis X_A is perpendicular to the longitudinal axis X_L and/or perpendicular to the first rotation axis X_R. The first rotation axis X_R is arranged between the first end 6 and a center C of the oral drug delivery device 202 along the longitudinal axis X_R, and the actuation axis X_A is arranged between the center C and the second end 8 along the longitudinal axis X_R.

The first body part 18 comprises a shaft 28 configured to engage with the first attachment part 12, the first attachment part 12 comprising a base 30 and a needle part 32, wherein the shaft 28 is arranged in a hinge cavity 33 of the base 30. The shaft 28/first body part 18 optionally engages with a first end part 35A of the first actuator 16A, and the base 30 engages with a second end part 35B of the first actuator 16A. For example, the first end part 35A may be inserted into a slit or engagement part 28A of the shaft 28.

The needle part 32 may be a two-part needle part as illustrated in drug delivery device 202 and has a first spike 32A arranged at the first distal end 14, the first spike 32A configured to penetrate a surface of a gastrointestinal tract. Further, the needle part 32 has a proximal section 32B and a distal section 32C with a bend 32D therebetween, the bend having a bending angle in the range from 60 degrees to 135 degrees. The distal section 32C is glued or otherwise attached to the proximal section 32B.

The second body part 20 optionally comprises a locking element 34 configured to engage the first attachment part 12, such as the base 30, and lock, in the initial position of the second body part, the first attachment part 12, i.e. prevent rotation of the first attachment part 12 about the first rotation axis X_R, e.g. at least in one direction. The lock element(s) 34 and corresponding lock part(s) 30B of the base 30 are configured via angled surfaces thereof to apply, from the first actuator 16A, an outward force to the second body part 20, such that the second body part is forced and moved along the first rotation axis to weak and/or break the cover before and/or during rotation of the first attachment part 12.

The oral drug delivery device 202, such as the second body part 20, optionally comprises a stop member (not shown) for controlling rotation of the first attachment part about the first rotation axis. The stop member denoted with ref 38 in other figures may be configured as a rotational stop for the first attachment part 12. In other words, the stop member may limit rotation of the first attachment part 12 to a maximum rotation angle, e.g. in the range from 180 degrees to 350 degrees.

The first body part 18 forms a first side wall 10A and an end part 10C of the body, and the second body part 20 forms a second side wall 10B of the body 10 with the first attachment part 12 in the initial position extending between the first side wall 10A and the second side wall 10B of the body.

Figure 3D:
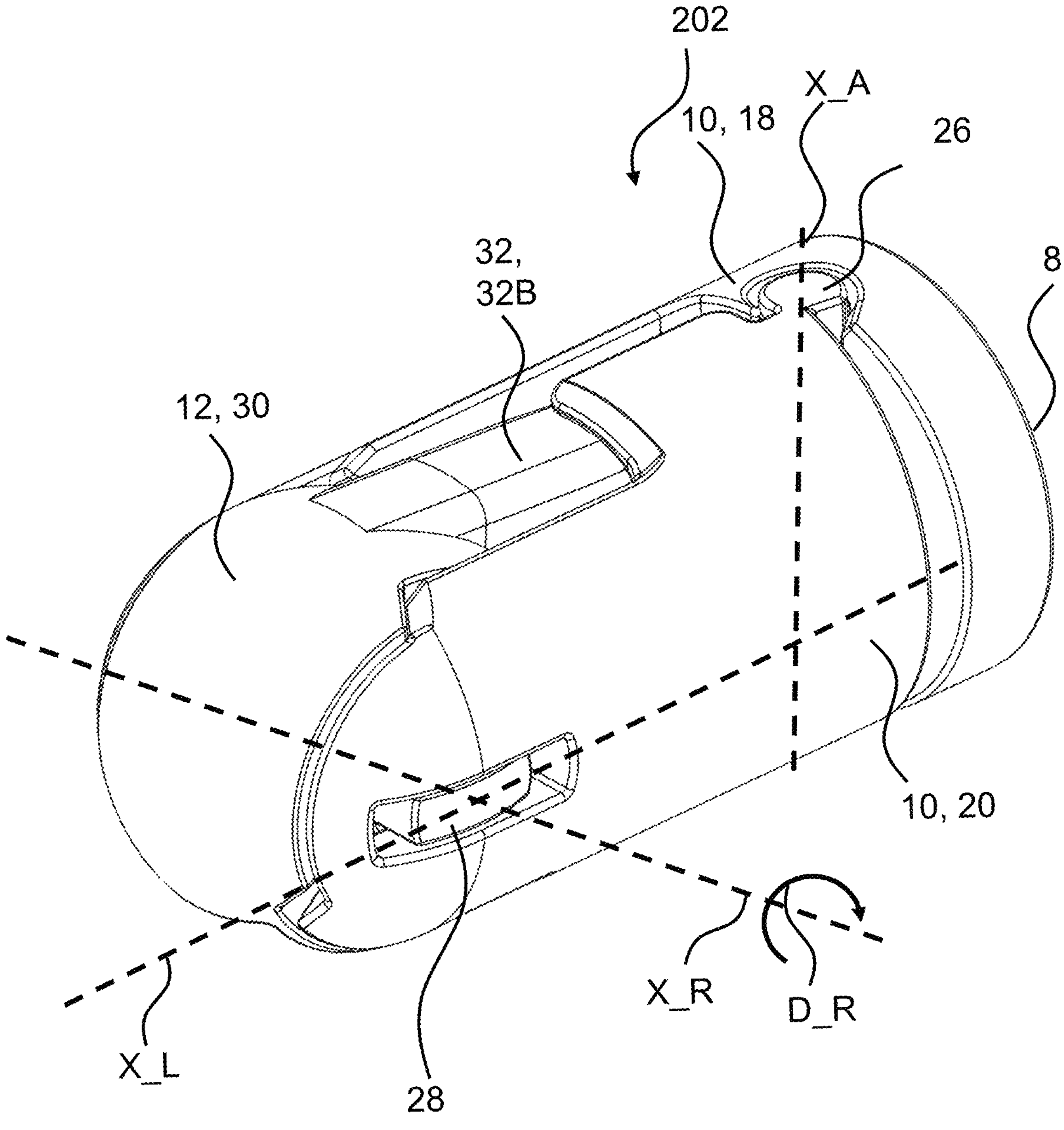
Figure 3E:
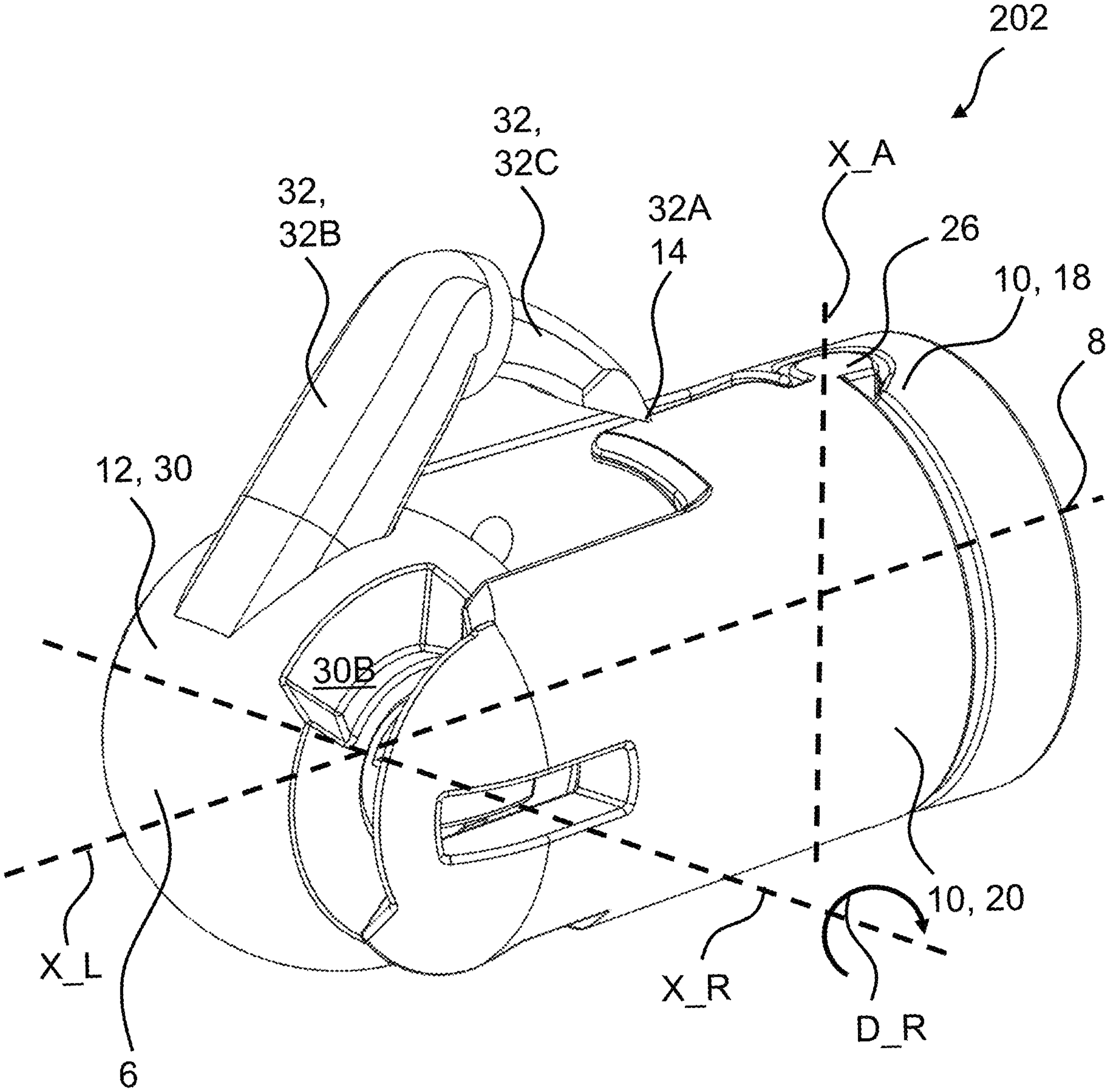

FIGS. 3D and 3E show perspective views of the oral drug delivery device 202 without cover 4. In FIG. 3C, the second body part 20 is in an initial position and kept in the initial position by cover 4. The first actuator 16A applies pressure to the second body part 20 via base 60 thereby weakening or breaking the cover 4 such that the second body 20 rotates about the actuation axis X_A to move the second body part 20 to a first position as shown in FIG. 3E in relation to the first body part 18 along the first rotation axis X_R. The movement from the initial position to the first position of the second body part 20 releases lock part(s) 30B and lock element(s) 34 and allows the first actuator 16A to rotate the first attachment part 12 further about the first rotation axis, such as in the range from 180 degrees to 350 degrees. The first attachment part 12 is configured to rotate more than 120 degrees from an initial position as in FIGS. 1A-1E to a first position about the first rotation axis X_R in the direction indicated by arrow D_R.

FIG. 3E shows a perspective view of the oral drug delivery device 202 without cover 4. The second body part 20 has been rotated about the actuation axis X_A thereby breaking or weakening the cover due to force from the first actuator via angled surfaces of lock part 30B and locking element 34. Further, the first attachment part 12 has been to rotated about the rotation axis X_R due to rotational force from the first actuator. The three axes X_R, X_L, and X_A are orthogonal, however variations such as ±30 degrees between the axes may be implemented.

Figure 4A:
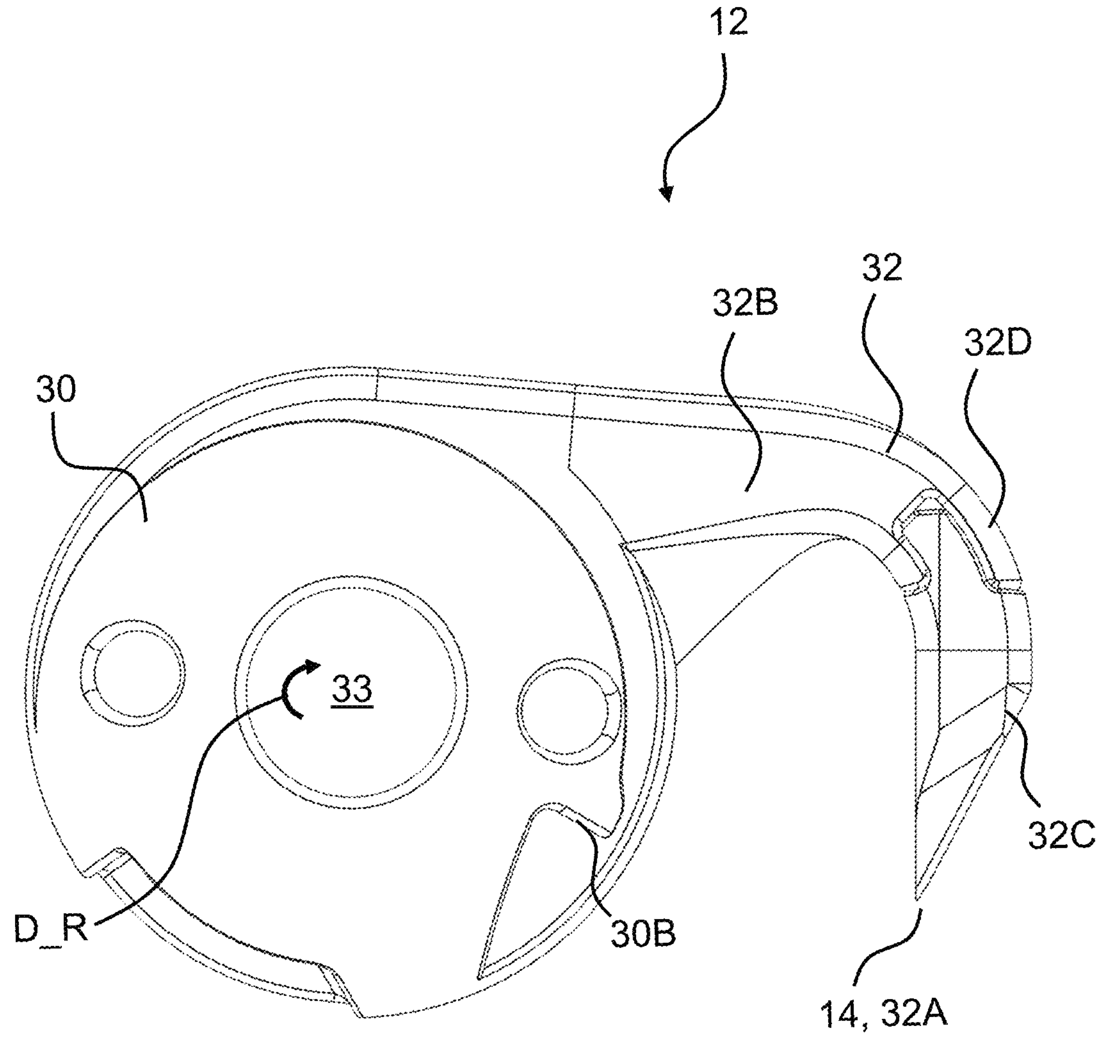
FIGS. 4A-4B show different views of an example first attachment part.
Figure 4B:
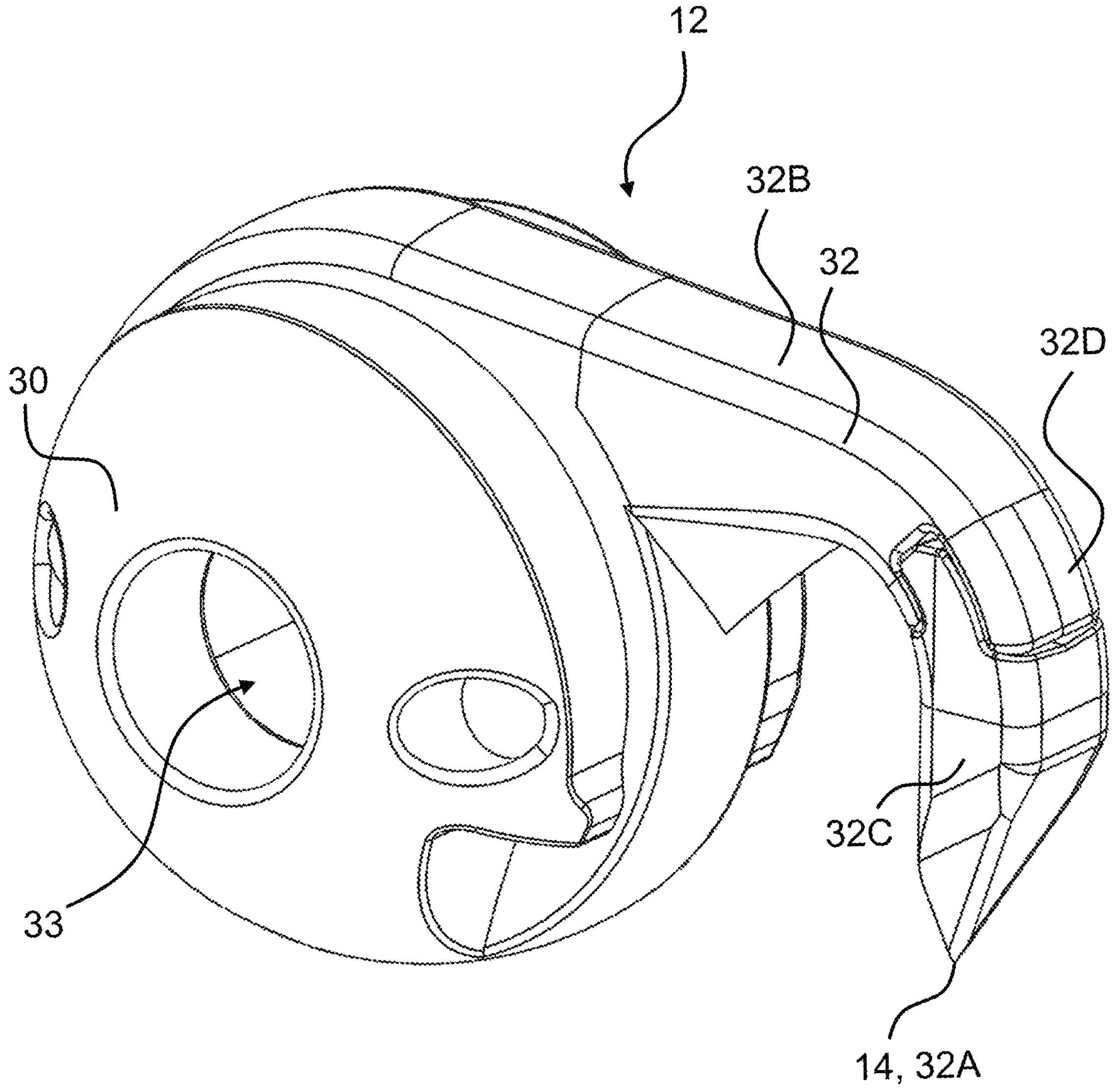

FIGS. 4A-4B show an example first attachment part 12. The first attachment part 12 may be implemented in any one of oral drug delivery devices 2, 102, 202, 302, 402. The first attachment part 12 has a first distal end 14 and comprises a base 30 and a needle part 32.

The base 30 optionally comprises a stop part 30A configured to engage with a stop member of oral drug delivery device for controlling rotation of the first attachment part in relation to a body of oral drug delivery device. The base 30 may comprise a lock part 30B configured to engage with a locking element, e.g. of a second body part, of oral drug delivery device. The needle part 32 has a first spike 32 at the distal end 32A, the needle part 32 comprising a proximal section 32B attached to the base 30. Further, the needle part 32 comprises a distal section 32C with a bend 32D between the proximal section 32B and the distal section 32C. The distal section 32C may be attached to the proximal section 32B via a mechanical coupling as illustrated and/or may be fixed, such as glued or welded, to the proximal sections, see also FIG. 3A-3E. The bend 32D optionally has a bending angle of 90±10 degrees to facilitate attachment during rotation of the first attachment part 12. The first attachment part 12 is made from one or more polymers. In one or more examples, an active drug substance is embedded in a material of the needle part 32, such as the distal section 32B, and/or arranged in a drug cavity 46 of the first attachment part 12/needle part 32, e.g. in the distal section 32B. The proximal section and the distal section may be made of different materials.

Figure 5A:
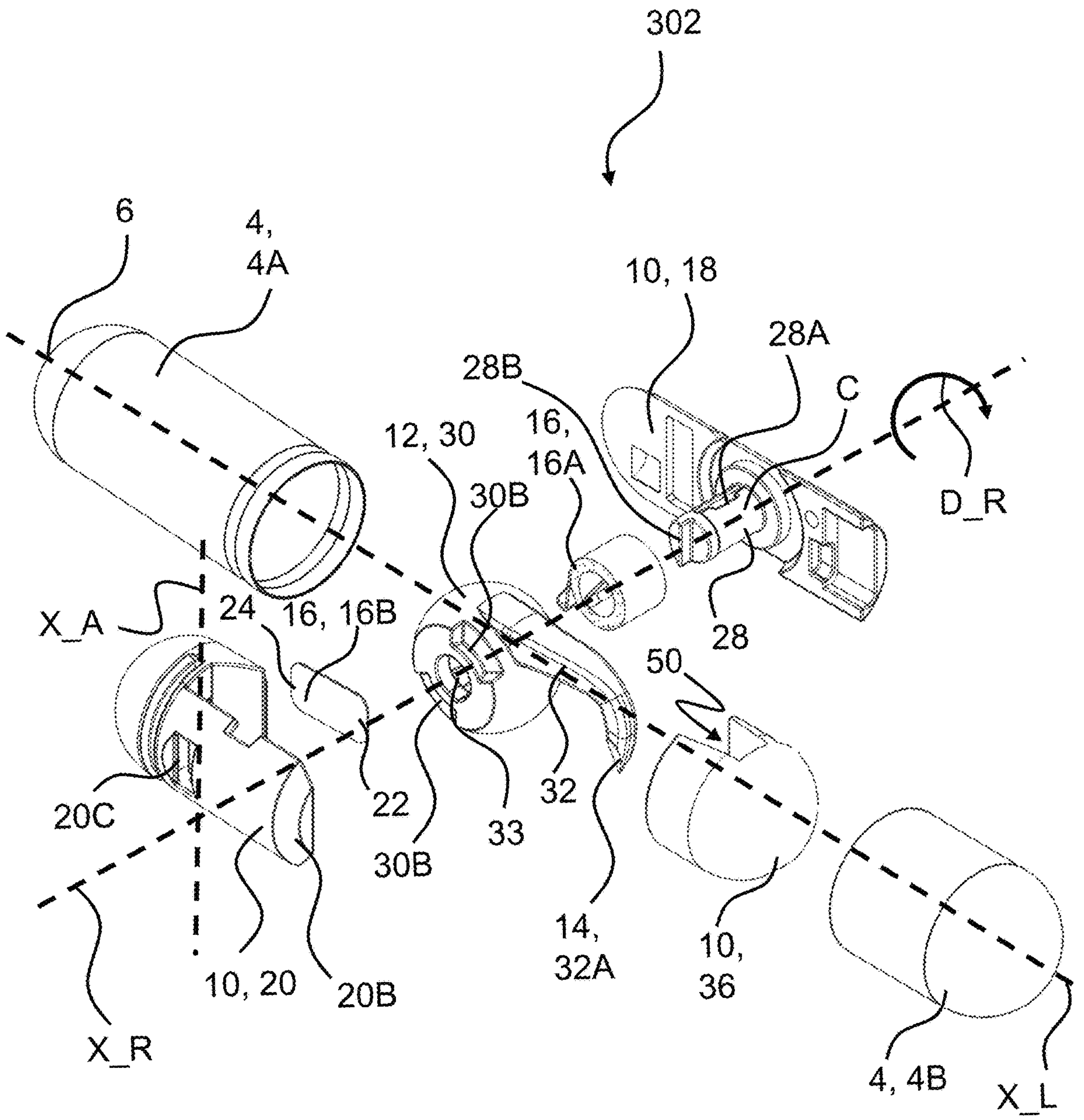
FIGS. 5A-5E show different views of an example oral drug delivery device.

FIGS. 5A-5E show different views of an example oral drug delivery device. FIG. 5A shows an exploded view of oral drug delivery device 302 comprising a cover 4 including a first cover part 4A and a second cover part 4B. The oral drug delivery device 302 has or defines a longitudinal axis X_L and extends from a first end 6 to a second end 8. The oral drug delivery device 302 comprises a body 10; a first attachment part 12 having a first distal end 14 and configured to deliver an active drug substance; and an actuator mechanism 16 engaged with the first attachment part 12 and configured to rotate the first attachment part 12, e.g. in the range from 135 degrees to 180 degrees, about a first rotation axis X_R perpendicular to the longitudinal axis X_L and thus forming an angle larger than 45 degrees with the longitudinal axis X_L. The first rotation axis X_R is arranged at a first distance in the range from 0.4 L to 0.6 L from the first end as illustrated at a center of the oral drug delivery device along the longitudinal axis X_L, wherein L is the length of the oral drug delivery device from the first end 6 to the second end 8. A centered first rotation axis allows for less rotation, e.g. less than 180 degrees, for attachment to the gastrointestinal tract thereby reducing the rotational length requirements for the first actuator.

The oral drug delivery device 302 is optionally configured to break or weaken the cover 4, such as first cover part 4A and/or second cover part 4B, prior to or during rotation of the first attachment part 12.

The actuator mechanism 16 comprises a first actuator 16A and optionally a second actuator 16B. The first actuator 16A is a coiled blade spring and is configured to rotate the first attachment part 12 about the first rotation axis X_R. The second actuator 16B is a blade spring or elastic element and may be configured to break or weaken the cover 4, such as first cover part 4A and/or second cover part 4B.

The body 10 comprises a first body part 18 and a second body part 20, and the actuator mechanism 16/second actuator 16B is configured to move at least a part of the second body part 20 in relation to the first body part 18 to break or weaken the cover 4 prior to or during rotation of the first attachment part 12.

The second actuator 16B has a first end 22 and a second end 24, the first end 22 engaging the first body part 18 at shaft end 28B and the second end 24 engaging the second primary body part 20B by insertion the of second actuator 16B in actuator slit 20C of the second primary body part 20B. Thereby, the actuator mechanism 16/second actuator 16B is configured to move the second primary body part 20B in relation to the first body part by moving the second body part 20/second primary body part 20B in relation to the first body part 18 along the first rotation axis X_R, see also FIG. 6.

The second body part 20 comprises an actuation joint 26 with an actuation axis X_A. The second actuator 16B is configured to rotate a second primary body part 20B of the second body part 20 in relation to the first body part 18 about the actuation axis X_A. The actuation axis X_A may be perpendicular to the longitudinal axis X_L and/or perpendicular to the first rotation axis X_R. The actuation axis X_A is arranged between the first end 6 and the center C along the longitudinal axis X_L.

The first body part 18 comprises a shaft 28 configured to engage with the first attachment part 12, the first attachment part 12 comprising a base 30 and a needle part 32, wherein the shaft 28 is arranged in a hinge cavity 33 of the base 30. The shaft 28 optionally engages with a first end part 35A of the first actuator 16A, and the base 30 engages with a second end part 35B of the first actuator 16A for allowing the first actuator 16A to rotate the first attachment part 12 in the rotation direction indicated with arrow D_R.

The needle part 32 has a first spike 32A arranged at the first distal end 14, the first spike 32A configured to penetrate a surface of a gastrointestinal tract. Further, the needle part 32 has a proximal section and a distal section with a bend therebetween, the bend having a bending angle in the range from 60 degrees to 135 degrees. The needle part 32 is optionally made from a biodegradeable and biodissolvable material.

The second body part 20 optionally comprises a locking element (not shown) configured to engage the first attachment part 12, such as the base 30/lock part(s) 30B, and lock, in the initial position of the second body part, the first attachment part 12, i.e. prevent rotation of the first attachment part 12 about the first rotation axis X_R in the rotation direction D_R.

The body 10 is a multi-part body and optionally comprises a third body part 36. The third body part 36 may engage with the first body part 18. The third body part 36 optionally comprises or forms a spike cavity 50 for accommodating the first distal end 14 in the initial position of the first attachment part.

The first body part 18 forms a first side wall 10A of the body, and the second body part 20 forms a second side wall 10B of the body 10 with the first attachment part 12 in the initial position extending between the first side wall 10A and the second side wall 10B of the body. The second body part 20 and the third body part 36 respectively forms an end part 10C.

Figure 5B:
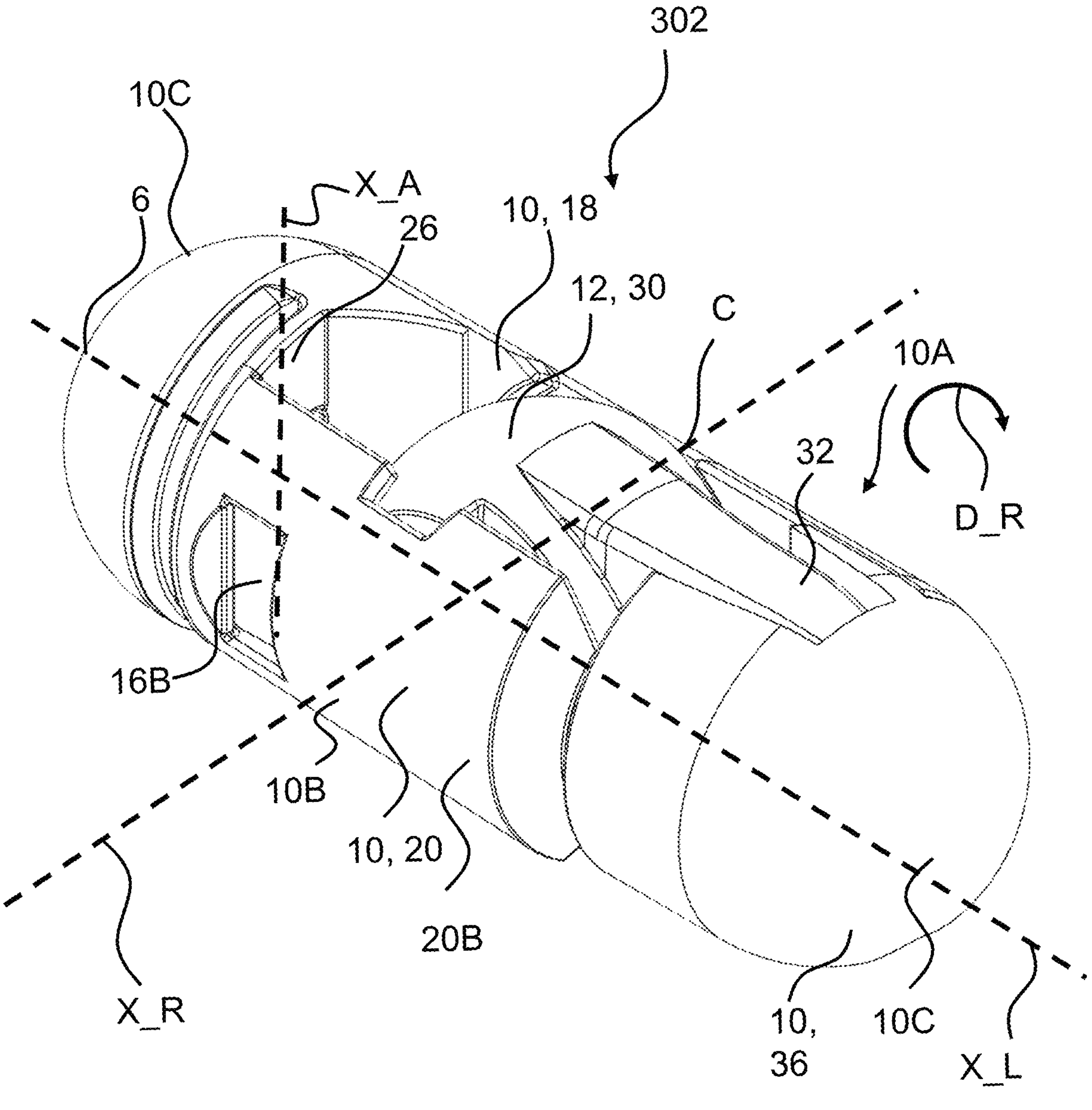

FIG. 5B shows a perspective view of the oral drug delivery device 302 without the cover in the initial position.

Figure 5C:
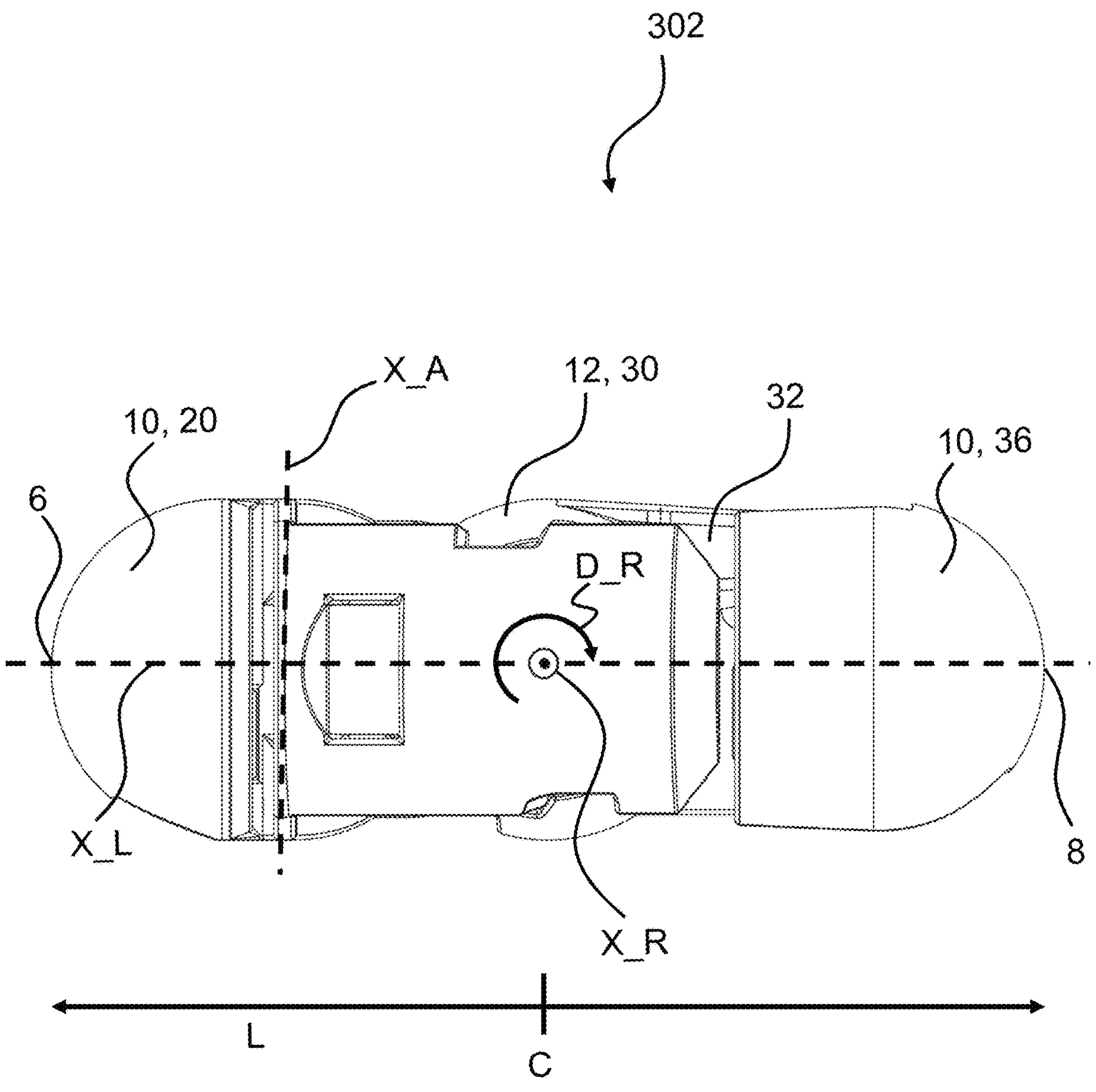

FIG. 5C shows a side view of the oral drug delivery device 302 without the cover in the initial position. The first rotation axis X_R is arranged at the center C of the oral drug delivery device, i.e. at a first distance of 0.5 L from the first end 6 along the longitudinal axis.

In FIGS. 5B and 5C, the second body part 20 is in an initial position and kept in the initial position by cover (not shown). In the initial position, locking element (not shown) of the second body part 20 engages with the first attachment part 12/base 30 and prevents rotation of the first attachment part 12 about the first rotation axis X_R. The second actuator applies pressure to the second body part 20 whereby a second primary part 20B of the second body 20 is rotated about actuation joint 26/actuation axis X_A to move the second primary body part 20B to a first position along the first rotation axis X_R thereby weakening or breaking the cover 4. The movement from the initial position to the first position of the second body part/second primary body part 20B, results in locking element(s) 34 of the second body 20 disengaging with the first attachment part 12/lock part(s) 30B of base 30, whereby the first actuator 16A is able to rotate the first attachment part 12 about the first rotation axis, e.g. more than 100 degrees, such as in the range from 120 degrees to 180 degrees.

In the oral drug delivery device 302, rotation of the first attachment part 12 is optionally triggered by a movement of the second primary body part 20B from an initial position shown in FIGS. 5B/5C to a first position in relation to the first body part 18. The first attachment part 12 is configured to rotate more than 120 degrees from an initial position as in FIGS. 5B-5C to a first position about the first rotation axis X_R in the direction indicated by arrow D_R.

Figure 5D:
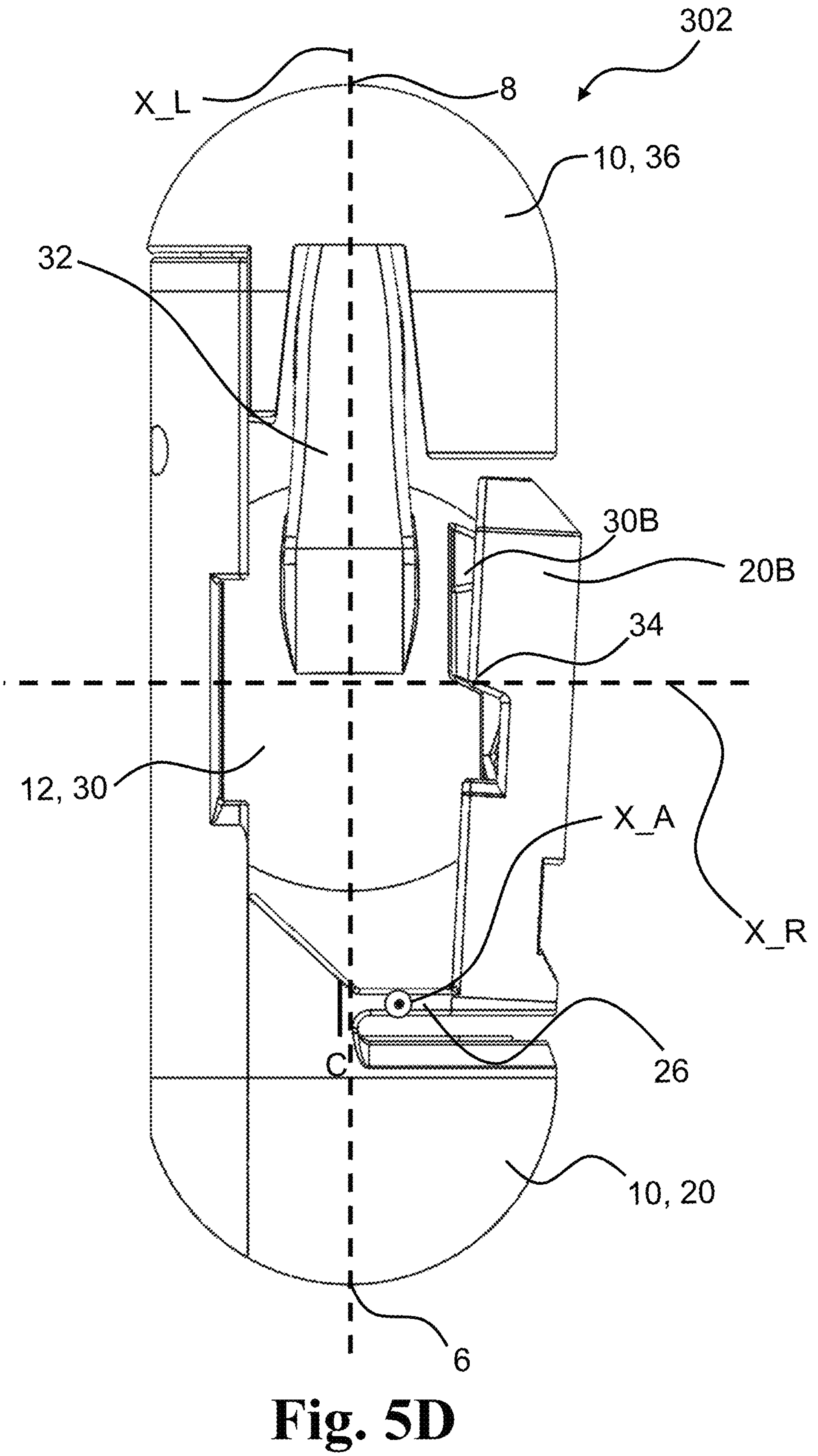

FIG. 5D shows a top view of the oral drug delivery device 302 without cover. The second primary body part 20B has been rotated about the actuation axis X_A thereby breaking or weakening the cover due to force from the second actuator. Further, the locking element 34 has disengaged from the first attachment part 12/lock part 30B of base thereby allowing the first attachment part 12 to rotate about the rotation axis X_R due to rotational force from the first actuator. The three axes X_R, X_L, and X_A are orthogonal, however variations such as ±30 degrees between the axes may be implemented.

Figure 5E:
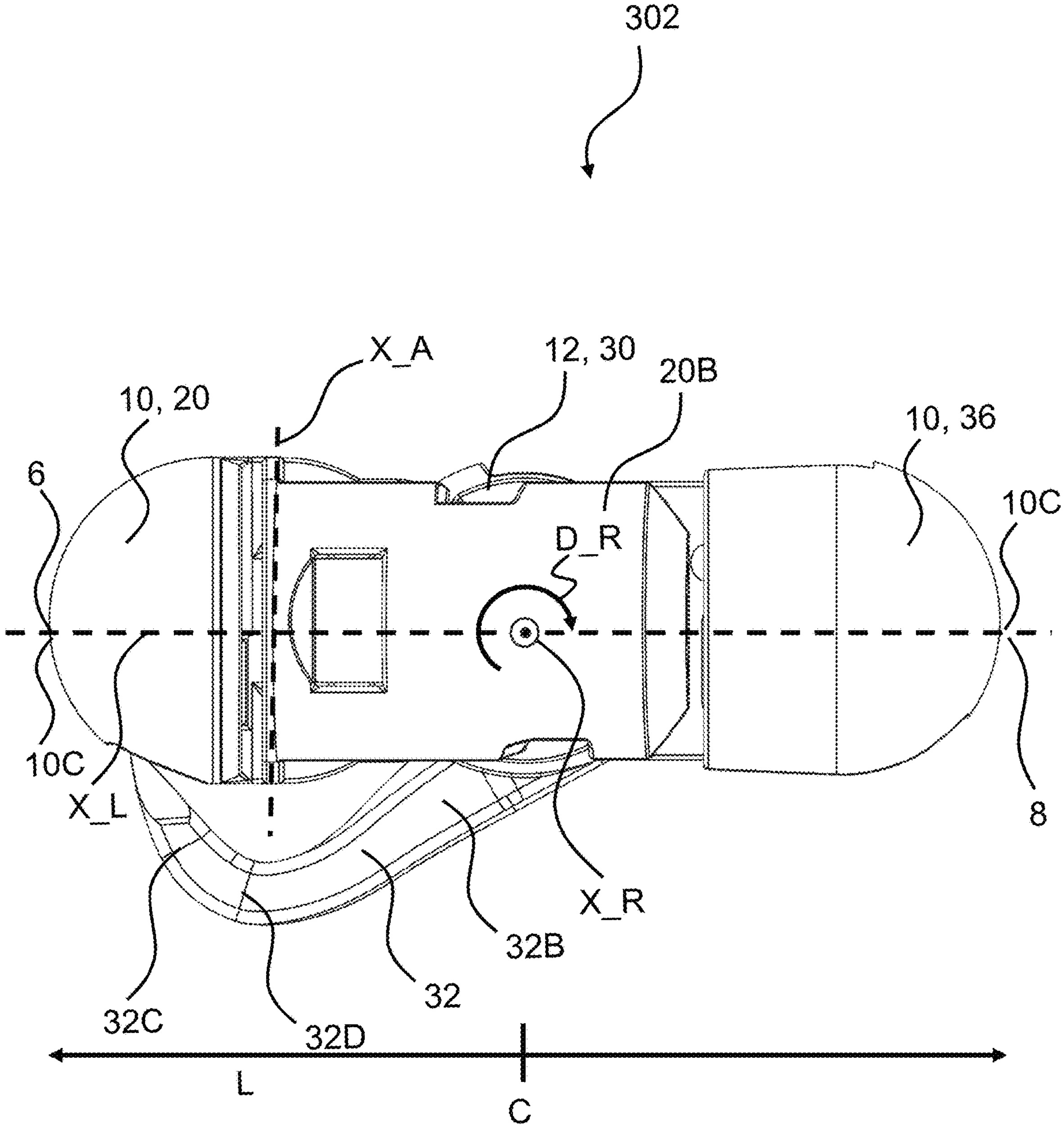

FIG. 5E shows a side view of the oral drug delivery device 302 without cover, where the first attachment part 12 has been rotated to a first position about the first rotation axis X_R, e.g. more than 100 degrees, such as in the range from 135 degrees to 180 degrees as illustrated in FIG. 5E, where the first rotation part 12 has been rotated about 150 degrees from the initial position to the first position. In order to initiate the rotation of the first attachment part 12, the second actuator 16B has moved the second primary body part 20B along the first rotation axis X_R thereby breaking or weakening the cover due to force from the second actuator 16B.

Further, the locking element 34 of the second primary body part 20B has disengaged from the lock part 30B of base 30 thereby allowing the first attachment part 12 to rotate about the rotation axis X_R due to rotational force from the first actuator 16A. The second body part 20B optionally acts as a stop member for the first distal 14 to stop the rotation of the first attachment part 12 in the first position.

Figure 6:
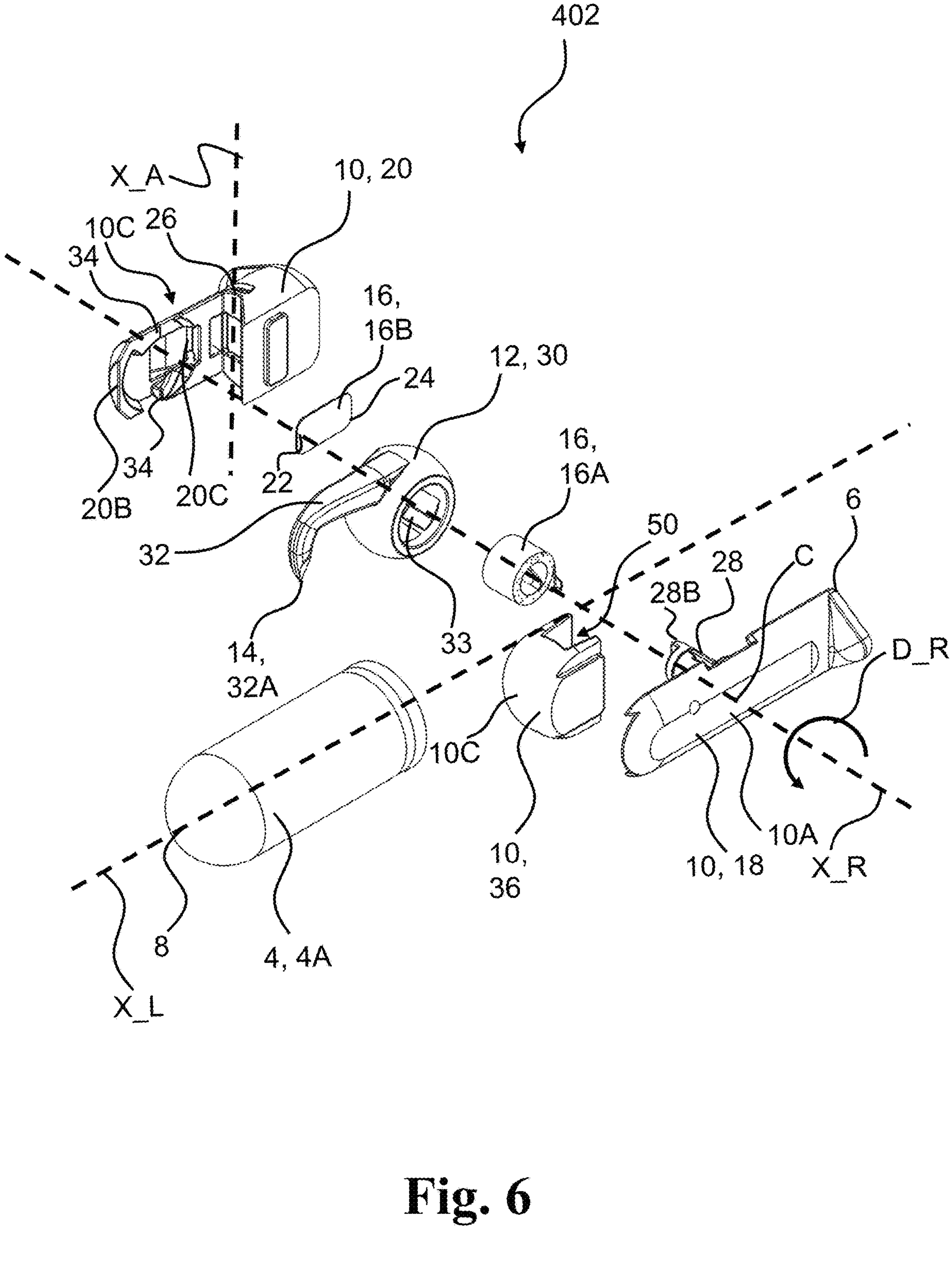
FIG. 6 shows an exploded view of an example oral drug delivery device.

FIG. 6 shows an exploded view of oral drug delivery device 402 comprising a single-part cover 4 with first cover part 4A covering more than 70% of the body part. The oral drug delivery device 402 has or defines a longitudinal axis X_L and extends from a first end 6 to a second end 8. The oral drug delivery device 402 comprises a body 10; a first attachment part 12 having a first distal end 14 and configured to deliver an active drug substance; and an actuator mechanism 16 engaged with the first attachment part 12 and configured to rotate the first attachment part 12, e.g. in the range from 135 degrees to 180 degrees, about a first rotation axis X_R perpendicular to the longitudinal axis X_L. The first rotation axis X_R is arranged at a first distance in the range from 0.4 L to 0.6 L from the first end as illustrated at a center C of the oral drug delivery device along the longitudinal axis X_L, wherein L is the length of the oral drug delivery device from the first end 6 to the second end 8.

The oral drug delivery device 402 is optionally configured to break or weaken the cover 4 prior to or during rotation of the first attachment part 12.

The actuator mechanism 16 comprises a first actuator 16A and optionally a second actuator 16B. The first actuator 16A is a coiled blade spring and is configured to rotate the first attachment part 12 about the first rotation axis X_R. The second actuator 16B is a blade spring and may be configured to break or weaken the cover 4, such as first cover part 4A and/or second cover part 4B.

The body 10 comprises a first body part 18 and a second body part 20, and the actuator mechanism 16/second actuator 16B is configured to move at least a part of the second body part 20 in relation to the first body part 18 to break or weaken the cover 4 prior to or during rotation of the first attachment part 12.

The second actuator 16B has a first end 22 and a second end 24, the first end 22 engaging the first body part 18 at shaft end 28B and the second end 24 engaging actuator slit 20 of the second primary body part 20B. Thereby, the actuator mechanism 16/second actuator 16B is configured to move the second body part 20 in relation to the first body part by moving the second body part 20 in relation to the first body part 18 along the first rotation axis X_R.

The second body part 20 comprises an actuation joint 26 with an actuation axis X_A. The second actuator 16B is configured to rotate a second primary body part 20B of the second body part 20 in relation to the first body part 18 about the actuation axis X_A. The actuation axis X_A may be perpendicular to the longitudinal axis X_L and/or perpendicular to the first rotation axis X_R. The actuation axis X_A is arranged between the first end 6 and the center C along the longitudinal axis X_L.

The first body part 18 comprises a shaft 28 configured to engage with the first attachment part 12, the first attachment part 12 comprising a base 30 and a needle part 32, wherein the shaft 28 is arranged in a hinge cavity 33 of the base 30. The shaft 28 optionally engages with a first end part of the first actuator 16A, and the base 30 engages with a second end part of the first actuator 16A for allowing the first actuator 16A to rotate the first attachment part 12 in the rotation direction indicated with arrow D_R about the first rotation axis X_R as also described in relation to other figures. The first rotation axis X_R is arranged at the center C of the oral drug delivery device, i.e. at a first distance of 0.5 L from the first end 6 along the longitudinal axis.

The needle part 32 has a first spike 32A arranged at the first distal end 14, the first spike 32A configured to penetrate a surface of a gastrointestinal tract. Further, the needle part 32 has a proximal section and a distal section with a bend therebetween, the bend having a bending angle in the range from 60 degrees to 135 degrees. The needle part 32 is optionally made from a biodegradeable material. The needle part 32 may be implemented as any of the needle parts described herein.

The second body part 20 optionally comprises a locking element 34 configured to engage the first attachment part 12, such as the base 30/lock part(s) (not shown), and lock, in the initial position of the second body part, the first attachment part 12, i.e. prevent rotation of the first attachment part 12 about the first rotation axis X_R in the rotation direction D_R.

The body 10 is a multi-part body and optionally comprises a third body part 36. The third body part 36 may engage with the first body part 18. The third body part 36 comprises or forms a spike cavity 50 for accommodating the first distal end 14 in the initial position of the first attachment part 12.

In oral drug delivery 402, the second body part 20 is kept in the initial position by the cover 4. In the initial position of the second body part, locking element 34 of the second body part 20 engages with the first attachment part 12/base 30 and prevents rotation of the first attachment part 12 about the first rotation axis X_R. The second actuator 16B applies pressure to the second body part 20 whereby a second primary part 20B of the second body 20 is rotated about actuation joint 26/actuation axis X_A to move the second primary body part 20B to a first position along the first rotation axis X_R thereby weakening or breaking the cover 4. The movement from the initial position to the first position of the second body part/second primary body part 20B, results in locking element(s) 34 of the second body 20 disengaging with the first attachment part 12/lock part(s) 30B of base 30, whereby the first actuator 16A is able to rotate the first attachment part 12 about the first rotation axis, e.g. more than 100 degrees, such as in the range from 120 degrees to 180 degrees.

In the oral drug delivery device 402, rotation of the first attachment part 12 is optionally triggered by a movement of the second primary body part 20B from an initial position to a first position in relation to the first body part 18. The first attachment part 12 is configured to rotate more than 120 degrees, such as 140, 150, 160, 170, or 180 degrees from the initial position to a first position about the first rotation axis X_R in the direction indicated by arrow D_R.

The first body part 18 forms a first side wall 10A of the body, and the second body part 20 forms a second side wall 10B of the body 10 with the first attachment part 12 in the initial position extending between the first side wall 10A and the second side wall 10B of the body. The second body part 20 and the third body part 36 respectively forms an end part 10C of the body.

Disclosed are oral drug delivery devices according to any of the following items.

Item 1. An oral drug delivery device, the oral drug delivery having a longitudinal axis and extending from a first end to a second end, the oral drug delivery device comprising:

a cover;

a body;
a first attachment part or drug delivery member having a first distal end and configured to deliver an active drug substance; and
an actuator mechanism engaged with the first attachment part/drug delivery member and configured to rotate the first attachment part/drug delivery member about a first rotation axis forming an angle larger than 45 degrees with the longitudinal axis.

Item 2. Oral drug delivery device according to Item 1, wherein the oral drug delivery device is configured to break or weaken the cover prior to and/or during rotation of the first attachment part/drug delivery member.

Item 3. Oral drug delivery device according to any one of Items 1-2, wherein the actuator mechanism comprises a first actuator and a second actuator, the first actuator configured to rotate the first attachment part/drug delivery member about the first rotation axis, and the second actuator configured to break or weaken the cover.

Item 4. Oral drug delivery device according to any one of Items 1-3, wherein the body comprises a first body part and a second body part, wherein the actuator mechanism is configured to move the second body part in relation to the first body part to break or weaken the cover prior to or during rotation of the first attachment part/drug delivery member.

Item 5. Oral drug delivery device according to Item 4, wherein the actuator mechanism is configured to move the second body part in relation to the first body part by moving the second body part in relation to the first body part along the first rotation axis.

Item 6. Oral drug delivery device according to any one of Items 4-5, wherein the actuator mechanism is configured to rotate the second body part in relation to the first body part about an actuation axis, the actuation axis forming an angle with the first rotation axis larger than 45 degrees.

Item 7. Oral drug delivery device according to Item 6, wherein the first rotation axis is arranged between the first end and a center of the oral drug delivery device along the longitudinal axis, and the actuation axis is arranged between the center and the second end of the oral drug delivery device.

Item 8. Oral drug delivery device according to any one of Items 1-6, wherein the first rotation axis is arranged at a center of the oral drug delivery device along the longitudinal axis.

Item 9. Oral drug delivery device according to any one of Items 4-8, wherein the actuator mechanism is configured to move the second body part in relation to the first body part by moving the second body part in relation to the first body part along the longitudinal axis.

Item 10. Oral drug delivery device according to any one of Items 4-9, wherein rotation of the first attachment part/drug delivery member is triggered by a movement of the second body part from an initial position to a first position in relation to the first body part.

Item 11. Oral drug delivery device according to any one of Items 4-10, wherein the first body part comprises a shaft, the first attachment part comprising a base and a needle part, wherein the shaft is arranged in a hinge cavity of the base.

Item 12. Oral drug delivery device according to Item 11 as dependent on Item 3, wherein the first actuator comprises a spiral spring, a blade spring, or an elastic member having a first end engaging with the shaft.

Item 13. Oral drug delivery device according to any one of Items 11-12, wherein the needle part has a first spike arranged at the first distal end, the first spike configured to penetrate a surface of a gastrointestinal tract.

Item 14. Oral drug delivery device according to any one of Items 11-13, wherein the needle part has a proximal section and a distal section with a bend therebetween, the bend having a bending angle in the range from 60 degrees to 135 degrees.

Item 15. Oral drug delivery device according to any one of Items 1-14, wherein the first rotation axis is perpendicular to the longitudinal axis.

Item 16. Oral drug delivery device according to any one of Items 1-15 as dependent on Item 6, wherein the actuation axis is perpendicular to the longitudinal axis.

Item 17. Oral drug delivery device according to any one of Items 1-16, wherein the first attachment part/drug delivery member is configured to rotate more than 120 degrees from an initial position to a first position about the first rotation axis.

The use of the terms “first”, “second”, “third” and “fourth”, “primary”, “secondary”, “tertiary” etc. does not imply any particular order, but are included to identify individual elements. Moreover, the use of the terms “first”, “second”, “third” and “fourth”, “primary”, “secondary”, “tertiary” etc. does not denote any order or importance, but rather the terms “first”, “second”, “third” and “fourth”, “primary”, “secondary”, “tertiary” etc. are used to distinguish one element from another. Note that the words “first”, “second”, “third” and “fourth”, “primary”, “secondary”, “tertiary” etc. are used here and elsewhere for labelling purposes only and are not intended to denote any specific spatial or temporal ordering.

Furthermore, the labelling of a first element does not imply the presence of a second element and vice versa.

It is to be noted that the word “comprising” does not necessarily exclude the presence of other elements or steps than those listed.

It is to be noted that the words “a” or “an” preceding an element do not exclude the presence of a plurality of such elements.

It should further be noted that any reference signs do not limit the scope of the claims, that the example embodiments may be implemented at least in part by means of both hardware and software, and that several “means”, “units” or “devices” may be represented by the same item of hardware.

Language of degree used herein, such as the terms “approximately,” “about,” “generally,” and “substantially” as used herein represent a value, amount, or characteristic close to the stated value, amount, or characteristic that still performs a desired function or achieves a desired result. For example, the terms “approximately”, “about”, “generally,” and “substantially” may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. For example, within less than or equal to 10 wt./vol. % of, within less than or equal to 5 wt./vol. % of, within less than or equal to 1 wt./vol. % of, within less than or equal to 0.1 wt./vol. % of, and within less than or equal to 0.01 wt./vol. % of the stated amount.

Although features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES

2, 102, 202, 302, 402 oral drug delivery device
4 cover
4A first cover part
4B second cover part
6 first end of drug delivery device
8 second end of drug delivery device
10 body
10A first side wall of body
10B second side wall of body
10C end part of body
12 first attachment part
13 drug delivery member
14 first distal end
16 actuator mechanism
16A first actuator
16B second actuator
18 first body part
18A first joint part
20 second body part
20A second joint part
20B second primary body part
20C actuator slit or seat
22 first end of second actuator
24 second end of second actuator
26 actuation joint
28 shaft
28A slit or engagement part of shaft
28B shaft end
30 base
30A stop part of base
30B lock part of base
32 needle part
32A first spike
32B proximal section
32C distal section
32D bend
33 hinge cavity
34 locking element
35A first end part of first actuator
35B second end part of first actuator
36 third body part
38 stop member
38A stop part
40 recess
42 through-going bore
44 plug
46 drug cavity
50 spike cavity
X_A actuation axis
X_L longitudinal axis
X_R rotation axis, first rotation axis

The invention claimed is:

1. An oral drug delivery device, the oral drug delivery having a longitudinal axis and extending from a first end to a second end, the oral drug delivery device comprising:
- a cover;
- a body;
- a first attachment part having a first distal end and configured to deliver an active drug substance; and
- an actuator mechanism engaged with the first attachment part and configured to rotate the first attachment part about a first rotation axis forming an angle larger than 45 degrees with the longitudinal axis,
- the oral drug delivery device configured to break or weaken the cover prior to or during rotation of the first attachment part, wherein body comprises a first body part and a second body part, wherein the actuator mechanism comprises a spring and is configured to move the second body part in relation to the first body part to break or weaken the cover prior to or during rotation of the first attachment part,
- wherein the actuator mechanism is configured to rotate the second body part in relation to the first body part about an actuation axis, the actuation axis forming an angle with the first rotation axis larger than 45 degrees.

2. The oral drug delivery device according to claim 1, wherein the actuator mechanism comprises a first actuator and a second actuator, the first actuator configured to rotate the first attachment part about the first rotation axis, and the second actuator configured to break or weaken the cover.

3. The oral drug delivery device according to claim 1, wherein the actuator mechanism is configured to move the second body part in relation to the first body part by moving the second body part in relation to the first body part along the first rotation axis.

4. The oral drug delivery device according to claim 1, wherein the first rotation axis is arranged between the first end and a center of the oral drug delivery device along the longitudinal axis, and the actuation axis is arranged between the center and the second end of the oral drug delivery device.

5. The oral drug delivery device according to claim 1, wherein the first rotation axis is arranged at a center of the oral drug delivery device along the longitudinal axis.

6. The oral drug delivery device according to claim 1, wherein the actuator mechanism is configured to move the second body part in relation to the first body part by moving the second body part in relation to the first body part along the longitudinal axis.

7. The oral drug delivery device according to claim 1, wherein rotation of the first attachment part is triggered by a movement of the second body part from an initial position to a first position in relation to the first body part.

8. The oral drug delivery device according to claim 1, wherein the first body part comprises a shaft, the first attachment part comprising a base and a needle part, wherein the shaft is arranged in a hinge cavity of the base.

9. The oral drug delivery device according to claim 8, the actuator mechanism comprising a first actuator, the first actuator configured to rotate the first attachment part about the first rotation axis, wherein the first actuator comprises a spiral spring, a blade spring, or an elastic member having a first end engaging with the shaft.

10. The oral drug delivery device according to claim 8, wherein the needle part has a first spike arranged at the first distal end, the first spike configured to penetrate a surface of a gastrointestinal tract.

11. The oral drug delivery device according to claim 8, wherein the needle part has a proximal section and a distal section with a bend therebetween, the bend having a bending angle in the range from 60 degrees to 135 degrees.

12. The oral drug delivery device according to claim 1, wherein the first rotation axis is perpendicular to the longitudinal axis.

13. The oral drug delivery device according to claim 1, wherein the first attachment part is configured to rotate more than 120 degrees from an initial position to a first position about the first rotation axis.

14. An oral drug delivery device, the oral drug delivery having a longitudinal axis and extending from a first end to a second end, the oral drug delivery device comprising:

a cover;

a body;

a first attachment part having a first distal end and configured to deliver an active drug substance; and an actuator mechanism engaged with the first attachment part and configured to rotate the first attachment part about a first rotation axis forming an angle larger than 45 degrees with the longitudinal axis, the oral drug delivery device configured to break or weaken the cover prior to or during rotation of the first attachment part, wherein body comprises a first body part and a second body part, wherein the actuator mechanism comprises a spring and is configured to move the second body part in relation to the first body part to break or weaken the cover prior to or during rotation of the first attachment part, wherein the first body part comprises a shaft, the first attachment part comprising a base and a needle part, wherein the shaft is arranged in a hinge cavity of the base.

15. The oral drug delivery device according to claim 14, wherein the first rotation axis is perpendicular to the longitudinal axis.

16. An oral drug delivery device, the oral drug delivery having a longitudinal axis and extending from a first end to a second end, the oral drug delivery device comprising:

a cover;

a body;

a first attachment part having a first distal end and configured to deliver an active drug substance; and an actuator mechanism engaged with the first attachment part and configured to rotate the first attachment part about a first rotation axis forming an angle larger than 45 degrees with the longitudinal axis, the oral drug delivery device configured to break or weaken the cover prior to or during rotation of the first attachment part, wherein body comprises a first body part and a second body part, wherein the actuator mechanism comprises a spring and is configured to move the second body part in relation to the first body part to break or weaken the cover prior to or during rotation of the first attachment part, wherein the actuator mechanism is configured to rotate the second body part in relation to the first body part about an actuation axis, the actuation axis forming an angle with the first rotation axis larger than 45 degrees, and wherein the actuation axis is perpendicular to the longitudinal axis.

17. The oral drug delivery device according to claim 16, wherein the first rotation axis is perpendicular to the longitudinal axis.

* * * * *